US009606126B2

(12) United States Patent
Wiener et al.

(10) Patent No.: US 9,606,126 B2
(45) Date of Patent: Mar. 28, 2017

(54) COMPOSITIONS AND METHODS FOR MEMBRANE PROTEIN DETERGENT STABILITY SCREEN

(75) Inventors: Michael C. Wiener, Charlottesville, VA (US); James M. Vergis, Gaithersburg, MD (US)

(73) Assignee: University of Virgina Patent Foundation, Charlottesville, VA (US)

( * ) Notice: Subject to any disclaimer, the term of this patent is extended or adjusted under 35 U.S.C. 154(b) by 1382 days.

(21) Appl. No.: 13/376,729

(22) PCT Filed: Jun. 29, 2010

(86) PCT No.: PCT/US2010/040347
§ 371 (c)(1),
(2), (4) Date: Dec. 7, 2011

(87) PCT Pub. No.: WO2011/008528
PCT Pub. Date: Jan. 20, 2011

(65) Prior Publication Data
US 2012/0108463 A1    May 3, 2012

Related U.S. Application Data
(60) Provisional application No. 61/221,198, filed on Jun. 29, 2009.

(51) Int. Cl.
G01N 33/68     (2006.01)
C30B 7/08      (2006.01)
B01D 15/38     (2006.01)

(52) U.S. Cl.
CPC .......... *G01N 33/6803* (2013.01); *C30B 7/08* (2013.01); *B01D 15/3804* (2013.01)

(58) Field of Classification Search
CPC .................................................. C40B 30/04
USPC .......................................................... 506/9
See application file for complete search history.

(56) References Cited

U.S. PATENT DOCUMENTS

| | | | |
|---|---|---|---|
| 6,172,262 B1 | 1/2001 | McQuade et al. | |
| 6,267,935 B1 | 7/2001 | Hol et al. | |
| 6,599,441 B1 | 7/2003 | Chrislip et al. | |
| 6,916,455 B2 | 7/2005 | Segelke et al. | |
| 7,276,216 B2 | 10/2007 | Segelke et al. | |
| 7,300,520 B2 | 11/2007 | Kwong et al. | |
| 2005/0205005 A1 | 9/2005 | Hansen et al. | |
| 2005/0205006 A1 | 9/2005 | Segelke et al. | |
| 2009/0093617 A1 | 4/2009 | Shenoy et al. | |
| 2012/0065104 A1* | 3/2012 | Wiener et al. ............... | 506/12 |

FOREIGN PATENT DOCUMENTS

WO    WO0114407    3/2002

OTHER PUBLICATIONS

McLuskey, Karen et al, "A protocol for high through put methods for the expression and purification of inner membrane proteins." Mol. Memb. Biol. (2008) 25(8) p. 599-608.*
Kawate, Toshimitsu and Gouaux, Eric, "Flurescence detection size exclusion chromatography for precrytslliazation screening of intergral membrane proteins." Structure (2006) 14 p. 673-681.*
Jarvet, Juri et al, "Reverisble random coil to beta-sheet transition and the early stage of aggregation of the abeta(12-28) fragment from the alzheimer peptide." J. Am. Chem. Soc. (2000) 122 p. 4261-4268.*
Philo, John, "Analyzing aggregates of different sizes and types." Presentation from Alliance protein laboratories, 2004, available at http://www.ap-lab.com/wcbp_2004_talk_full.pdf.*
Homon, Cathy, ANSI news and publications press release, 2004, available at http://ansi.org/news_publications/news_story.aspx?menuid=7&articleid=4635c896f02c40c28de0b886fdc9c54d.*
Kavonian, Mark and Chernokalaskaya, Elena, "Ultrafiltration: trends in sample prep." Drug discovery and development (2007) p. 1-12.*
Song, Lanzhou and Gouaux, Eric, "Crystallization of the alpha-hemolysin heptamer solubilized in decyldimethyl and decyldiethylphosphine oxide." Acta Cryst (1998) D54, p. 276-278.*
Calbiochem 2006 catalog for biological detergents.*
Anatrace 2004 catalog of surfactants.*
Le Marie, Mark et al, "Interaction of membrane proteins and lipids with solubilizing detergents." Biochemica and Biophysica Acta (2000) 1508 p. 86-111.*
Keyes, Melvin H. et al, "Solubilizing detergents for membrane proteins." In Methods and results in creytallization of membrane proteins (2003), Iwata ed., ISBN 0-9636817-9-6.*
Yu, Seungju M. et al, "An improved tripod amphiphile for membrane protein solubilization." Protein Sci. (2000) 9 p. 2518-2527.*
Welling-Wester, Sytske et al, "Detergent extraction of herpes simplex virus type 1 glycoprotein d by zwitterionic and non-ionic detergetns and purification by ion exchange high performance liquid chromatography." J. Chrom. A (1998) 816 p. 29-37.*

(Continued)

*Primary Examiner* — Fred Reynolds
(74) *Attorney, Agent, or Firm* — Rodney L. Sparks

(57) ABSTRACT

The invention provides methods to assess protein stability and to obtain sizing information. In one aspect, the screen comprises a 94 detergent panel and a series of MWCO filtered microplates. A protein of interest is bound to an affinity matrix and aliquoted into a 96-well microplate. Wells containing the immobilized protein are washed in the new detergent and then eluted in the new detergent into a collection plate. Protein not stable in the new detergent is precipitated on the resin and not present in the elutions. Half of the elution is passed through a high (i.e., 300 kDa) MWCO microplate and the other half through a low (i.e., 100 kDa) MWCO microplate. Elutions from the microplates are spotted on a nitrocellulose membrane, visualized by Western analysis (or by some other method), and quantified. The high MWCO provides stability readout and the ratio of low/high kDa provides sizing information.

28 Claims, 6 Drawing Sheets

(56) References Cited

OTHER PUBLICATIONS

ICI pamphlet for selecting surfactants, The HLB system (1976) found at http://www.firp.ula.ve/archivos/historicos/76_Book_HLB_ICI.pdf.*
Psakis, Georgios et al, "Expression screening of integral membrane proteins from helicobacter pylori 26695." Protein Sci. (2007) 16 p. 2667-2676.*
Radaev, et al., "A Survey of protein-protein complex crystallizations", Acta Crystallogr D. Biol., Crystallogr. 2006, 62 (Pt. 6); 605-612.
Radaev, et al., "Crystallization of protein-protein complexes.", J. Appl. Cryst. 2002, 35:674-676.
Collins, et al., Crystallization Optimum Solubility Screening: using crystallization results to identify the optimal buffer for protein crystal formation. Acta Cryst. 2005, F61: 1035-1038.
Niegowski, et al., "A simple strategy towards membrane protein purification and crystallization", Int. J. Biol. Macromol. 39 (2005), pp. 83-87.
Kawate, et al., "Fluorescence-detection size exclusion chromatography for precrystallization screening of integral membrane proteins", Structure 14 (2006), pp. 673-681.
Wiener, et al., Existing and emergent roles for surfactants in the three-dimensional crystallization of integral membrane proteins. Curr. Opin. Colloid Interface Sci. 6 (2001), pp. 412-419.
Postis, et al., "A high-throughput assay of membrane protein stability", Molecular Membrane Biol., Dec. 2008; 25 (8): pp. 617-624.
Vergis, et al., "A high-throughput differential filtration assay to screen and select detergents for membrane proteins", Analytical Biochemistry 407 (2010), 1-11.

* cited by examiner

COMPOSITIONS AND METHODS FOR MEMBRANE PROTEIN DETERGENT STABILITY SCREEN

CROSS REFERENCE TO RELATED APPLICATIONS

This application is a national stage filing of International Application No. PCT/US2010/040347, filed Jun. 29, 2010, which claims priority under 35 U.S.C. §119(e) to U.S. Provisional Application Ser. No. 61/221,198 filed Jun. 29, 2009, the disclosure of which is incorporated by reference in its entirety herein.

STATEMENT REGARDING FEDERALLY SPONSORED RESEARCH OR DEVELOPMENT

This invention was made with government support under Grant No. 5R01 GM075931, awarded by The National Institutes of Health. The government has certain rights in the invention.

BACKGROUND

Membrane proteins comprise between 15% and 39% of the human proteome and 45% of drugs target these proteins. Membrane proteins are prevalent in the proteomes of pathogenic microorganisms and are the targets of many antimicrobial agents. Membrane proteins play essential roles in pathophysiology and the biology of all organisms. Near atomic resolution structures are required for our understanding of the function of these molecules. X-ray crystallography, electron crystallography, and nuclear magnetic resonance spectroscopy (NMR) are the currently available methods for obtaining high resolution structures of macromolecules, including membrane proteins.

Purified membrane proteins require surfactants, typically detergents, to remain soluble in an aqueous environment. The complex of the membrane protein and the associated detergent molecules (the protein detergent complex, PDC), is the object studied by x-ray crystallography or NMR.

The difficulties of working with membrane proteins are demonstrated by the fact that membrane protein structures represent less than 1% of the total number of protein structures in the Protein Data Bank, despite integral membrane proteins encompassing 15-30% of most genomes [1; 2; 3]. Technical challenges in membrane protein structure determination include expression (to obtain suitable amounts of protein), purification (to obtain suitably stable and functional protein), and sample preparation (to obtain suitable two-dimensional crystals for electron crystallography, three-dimensional crystals for x-ray crystallography, or solutions for NMR spectroscopy).

In preparation for structural (and other) studies, membrane proteins are extracted from their native lipid bilayer environment, and this membrane bilayer is replaced by a membrane-mimetic. The membrane-mimetic solute is almost always a detergent at a concentration above its critical micelle concentration (CMC), where the detergent surrounds the hydrophobic membrane-facing portion of the membrane protein and forms the protein-detergent complex (PDC). PDCs are in equilibrium with detergent micelles and monomers in this solution. The chemical-space of detergents is large, and the solution (and crystallization) properties of a membrane protein are intimately related to the properties of the detergent(s) comprising the PDC [4; 5]. In addition, the function of a membrane protein can be maintained at native or near-native levels or can be completely abrogated, depending upon the detergent composition of the PDC.

Currently, according to the Membrane Proteins of Known Structure database, 231 unique integral membrane protein structures have been solved by x-ray crystallography. The Membrane Protein Data Bank database [6] lists 864 non-unique membrane protein x-ray crystal structures, for which more than fifty different detergents have been used in their solubilization and/or crystallization. These detergents are not equally represented. For example, five detergents, n-dodecyl-β-D-maltopyranoside (DDM); n-decyl-β-D-maltopyranoside (DM); n-nonyl-β-D-glucopyranoside (NG); n-octyl-β-D-glucopyranoside (OG); and n-dodecyl-N,N-dimethylamine-N-oxide (LDAO) have yielded the majority of α-helical membrane protein structures [7].

While this speaks to the utility (and extensive use) of these five detergents, over 40% of the structures solved to date required detergents other than those five. As such, survey of membrane protein stability in "detergent-space" is an important aspect of membrane protein structural biology (and biochemistry).

There are several methods to test detergent solubility of membrane proteins. These methods include: gel filtration; dilution [5]; and the ultracentrifugation dispersity sedimentation assay [8]. Inspection of the gel filtration chromatogram has been routinely used for both soluble and membrane proteins to assess the quality of a protein.

The method of fluorescence-detection size-exclusion chromatography (FSEC) was an advance in gel filtration chromatography of integral membrane proteins [9]. The unique optical signal of a fluorescently-tagged recombinant protein enables that protein to be detected and characterized in a solubilized mixture, prior to purification. Also, the use of fluorescence (versus absorbance) detection increases the sensitivity by several orders of magnitude, requiring less solubilized (or purified) protein for the chromatography analysis. In order to evaluate detergent stability, gel filtration can be performed in either of two ways: 1) the column is equilibrated in the detergent to be tested and the protein is loaded onto the column ("detergent-specific mobile phase") or 2) the protein is exchanged into a new detergent and then injected onto a column equilibrated with a known "good" detergent for all chromatographic runs ("generic mobile phase").

The use of the generic mobile phase speeds up the gel filtration runs by eliminating the column washing and equilibration steps for the next detergent. The generic mobile phase method rests upon the assumption that if a protein sample has been exchanged into an incompatible detergent, then a compatible detergent in the mobile phase will not reverse the deleterious effects of that incompatible detergent [9].

Data from our lab suggests that this is not true for all cases, so we do not currently favor the generic mobile phase method. We note that the original FSEC publication [9] utilizes a generic mobile phase; however, fluorescence detection is equally applicable to use of a detergent-specific mobile phase. For the dilution method, concentrated protein is diluted into a new test detergent and the $Abs_{320}$ nm:$Abs_{280}$ nm ratio is recorded over time. Because $Abs_{320}$ nm is indicative of protein aggregation, an increase in this ratio is diagnostic of the protein not being stable in the new detergent [5]. In the ultracentrifugation dispersity sedimentation assay, the protein is concentrated, diluted into the test detergent buffer with three concentration/dilution steps, and finally allowed to incubate overnight. At that point, a sample is taken while the rest of the protein is spun in the ultracentrifuge to pellet any aggregated protein. Another protein sample is taken after ultracentrifugation and both the pre- and post-ultracentrifugation samples are run on SDS-PAGE and compared. Any difference in band intensity between the two samples is indicative of aggregated protein being removed during the intermediate ultracentrifugation step and thus related to detergent stability [8].

These three methods all possess shortcomings. The biggest limitation is that the methods described above are not detergent exchanges, but rather are detergent dilutions (the exception is the single case where the protein is already in the same detergent as that present in the gel filtration mobile phase). This is a problem if the initial detergent is not diluted to a concentration below its CMC or, in the case of gel filtration, if the original detergent's micelles are not separated from the protein-detergent complex (PDC), or if a mixed detergent population exists. In these instances, the presence of the original detergent can "protect" a protein from a destabilizing detergent resulting in false positives.

The original detergent's concentration is of great concern especially when the method utilizes an ultrafiltration concentration step of the protein since detergent micelles typically concentrate along with the protein even when a large molecular weight cut-off (MWCO) is used. Another limitation is that milligram amounts of protein and large amounts of expensive detergent reagents may be necessary, especially if there are a large number of conditions to be tested. Lastly, the time required to perform each method can be long, which usually limits the number of detergents surveyed, especially in the case of gel filtration where only one detergent can be tested at a time.

There is a long felt need in the art for compositions and methods useful as a system for efficiently determining conditions and the proper detergents for membrane proteins from solutions containing a membrane protein in a purified and soluble state. The present invention satisfies these needs.

SUMMARY OF THE INVENTION

The present invention pertains to the field of membrane protein biochemistry and structural biology. The assay technology developed and presented here focuses upon the selection of appropriate detergents for use with a specific membrane protein, which is a critical aspect of both purification and sample preparation. The screen of the present invention was developed to overcome shortcomings of current methods for detergent screening as well to expand the number of detergents examined.

The present invention encompasses a quick and robust method to assess membrane protein stability and to obtain rudimentary sizing information in a high throughput format. Various aspects and embodiments of the invention are described in further detail below.

The present invention provides compositions and methods useful for a new membrane protein detergent screening assay to determine stability and size of the protein.

The present invention provides a method for determining the stability and size of a protein in a test detergent. In one aspect, the method comprises obtaining a solution comprising a protein of interest in a first detergent and then adding an effective amount of an affinity resin to the solution. Then an aliquot of the solution comprising the protein in the first detergent and the affinity resin is added to a first chamber or well, wherein the chamber or well has a filter in it with a pore size of about 0.2 μm. Then, as a means of detergent exchange a wash solution comprising a different detergent (i.e., a test detergent) is used to wash away the first detergent in the first chamber. Up to about 20 column volumes of the different test detergent wash solution can be used. Then, the protein is eluted through the filter by using an elution solution prepared using the different test detergent and eluting the protein with up to about 6 column volumes of the elution solution. An aliquot of the eluate is then passed through a second chamber or well comprising a high molecular weight cut-off filter and another aliquot of the eluate is passed through a third chamber comprising a low molecular weight cut-off filter. Then, the amount of protein in each of the two eluates passing through the high and low molecular weight cut-off filters is determined and then compared by comparing the amount of protein eluted through the high molecular weight cut-off filter with the amount of protein eluted through the low molecular weight cut-off filter, thereby determining the stability and size of a protein in at least one detergent.

In one aspect, the filtration of the detergent mixtures in the chambers or wells can be enhanced by centrifuging the chambers or wells.

For determining sizing information of a protein, the present invention provides a differential filtration (DF) process using filters with different molecular weight cut-offs. In one embodiment, the high molecular weight cut-off filter is about 300 kDa and the low molecular weight cut-off filter is about 300 kDa.

In one embodiment, the chamber or well is part of a multiwell plate.

In one embodiment, the present invention provides a multiwell plate-based detergent screening assay, which is coupled with an assay for determining molecular weight ranges of the protein of interest. In one aspect, the multiwell plate is a microplate. The practice of the invention is not limited to a specific number of wells per plate. A plate may comprise multiple wells or chambers comprising an appropriate filter(s) for the process being performed. For example, the plate can be a 1 well, 6 well, 12 well, 24 well, 48 well, 96 well, 384 well, or 1536 well plate. In one aspect, the 96 well plate is an SBS format plate.

Multiple detergents can be used in the screening process and the number of detergents tested can be modified based on the number of wells or chambers in the plate or container being used (See Table 1).

In one embodiment, the assay comprises a panel of 94 detergents suitable for structural studies on membrane proteins and a set of labware that allows for the determination of both stability and rudimentary size the protein:detergent complex (PDC) to be obtained. This is a high throughput assay that utilizes microgram amounts and microliter volumes of reagents to obtain detergent stability information in approximately 2 hours. The present invention also encompasses using a different number of detergents than 94.

The method further allows for the use of low levels of protein. In one embodiment, about 1000 micrograms or less of a protein of interest is needed in the first detergent. In one aspect, about 500 micrograms or less, or about 400 micrograms or less, or about 200 micrograms or less, or about 100 micrograms or less, or about 50 micrograms or less of the protein can be used. Furthermore, if an appropriate, protein-specific detection method is used, the protein of interest can be screened in a crude, unpurified form.

The method is rapid and in some cases can be performed in less than about two hours. Protein amounts eluted through the high and low molecular weight can be determined by, for example, dot blot or Western blot analysis, wherein the amounts are measured and quantified by established techniques and methods. In one aspect, the high molecular weight cut-off dot blots, are normalized and plotted with the ratio of low:high normalized intensities and the values grouped into quartiles. In another aspect, the protein amounts determined from the high molecular weight cut-off dot blots are normalized and plotted graphically on the abscissa while the ratio of low:high normalized intensities are plotted on the ordinate.

The DF method alone can provide rudimentary sizing information of macromolecules without the need for gel filtration. DF can be performed using the described microplates, different sets of MWCO plates, or other formats in which MWCO filters are utilized (e.g., spin columns, ultrafiltration cell).

The compositions and methods of the invention are also useful, for example, to screen detergent mixtures, additives, ionic strength, and pH for soluble proteins as well.

In one aspect, the compositions and methods of the invention are useful for membrane proteins.

In one embodiment, the concentrations of the different detergents used are based on the critical micelle concentrations of the different detergents. In one aspect, the concentration used for a detergent is the critical micelle concentration.

In one embodiment, a detergent used in the invention has moderate or high aqueous solubility. In one embodiment, a detergent used in the invention has zwitterionic or nonionic headgroups.

The present invention further encompasses the preparation and use of a detergent panel and a kit using the detergents and controls described herein. In one aspect, other detergents can also be used. Additional kit and panel details are as follows:

Detergent Screening Kit—all of the necessary reagents to perform the detergent stability assay
  a. Detergent Stability Panel—microplate block containing the reagents of the detergent panel in 2× working concentrations.
  b. DF Microplates—set of filtered microplates required to perform the assay. The low and high plates display retention and passage properties suited to the practice of the present invention, but other plates and other molecular weight exclusion limits are encompassed as well. The present invention is not limited to the used of these two molecular weight cutoffs and that is why the terms "high" and "low" are also used, to ensure that the emphasis is on the fact that the plates are of different molecular weight cut-offs.

In one embodiment, at least one of the following detergents is used in a kit or panel or in the methods of the invention:

ZWITTERGENT® 3-12, ZWITTERGENT® 3-14, n-Decyl-N,N-dimethylglycine, n-Dodecyl-N,N-dimethylglycine, n-Decyl-N,N-dimethylamine-N-oxide, n-Undecyl-N,N,-dimethylamine-N-oxide, n-Dodecyl-N,N-dimethylamine-N-oxide, C-DODECAFOS™, CYCLOFOS™-4, CYCLOFOS™-5, CYCLOFOS™-6, CYCLOFOS™-7, FOS-CHOLINE®-10, FOS-CHOLINE®-11, FOS-CHOLINE®-12, FOS-CHOLINE®-13, FOS-CHOLINE®-14, FOS-CHOLINE®-ISO-11, FOS-CHOLINE®-ISO-11-6U, FOS-CHOLINE®-ISO-9, FOS-CHOLINE®-UNSAT-11-10, 1,2-Diheptanoyl-sn-glycero-3-phosphocholine, LysoPC-10, LysoPC-12, FOSFEN™-9, CHAPS, CHAPSO, n-Dodecyl-N,N-(dimethylammonio)undecanoate, n-Dodecyl-N,N-(dimethylammonio)butyrate, LAPAO, TRIPAO, TWEEN® 20, BRIJ®35, TRITON® X-100, TRITON® X-114, TRITON® X-305, TRITON® X-405, [Octylphenoxy]polyethoxyethanol, Dimethyloctylphosphine oxide, Dimethylnonylphosphine oxide, Dimethyldecylphosphine oxide, Dimethylundecylphosphine oxide, Dimethyldodecylphosphine oxide, *Triethylene glycol monohexyl ether, Tetraethylene glycol monohexyl ether, Pentaethylene glycol monohexyl ether, Pentaethylene glycol monoheptyl ether*, Tetraethylene glycol monooctyl ether, Pentaethylene glycol monooctyl ether, Hexaethylene glycol monooctyl ether, Pentaethylene glycol monodecyl ether, Hexaethylene glycol monodecyl ether, Polyoxyethylene(9)decyl ether, Octaethylene glycol monododecyl ether, Polyoxyethylene(9)dodecyl ether, Polyoxyethylene(10)dodecyl ether, Polyoxyethylene(8)tridecyl ether, Big CHAP, Big CHAP,deoxy, Genapol® X-100, n-Heptyl-β-D-thioglucopyranoside, n-Octyl-β-D-glucopyranoside, n-Nonyl-β-D-glucopyranoside, CYGLU®-3, HECAMEG, Hega®-9, C-Hega®-10, C-Hega®-11, CYMAL®-3, CYMAL®-4, CYMAL®-5, CYMAL®-6, CYMAL®-7, 2,6-Dimethyl-4-heptyl-β-D-maltoside, n-Octyl-β-D-maltopyranoside, n-Nonyl-β-D-maltopyranoside, n-Decyl-α-D-maltopyranoside, n-Decyl-β-D-maltopyranoside, n-Undecyl-α-D-maltopyranoside, n-Undecyl-β-D-maltopyranoside, ω-Undecylenyl-β-D-maltopyranoside, n-Dodecyl-α-D-maltopyranoside, n-Dodecyl-β-D-maltopyranoside, n-Tridecyl-β-D-maltopyranoside, n-Octyl-β-D-thiomaltopyranoside, n-Nonyl-β-D-thiomaltopyranoside, n-Decyl-β-D-thiomaltopyranoside, n-Undecyl-β-D-thiomaltopyranoside, n-Dodecyl-β-D-thiomaltopyranoside, Sucrose8, Sucrose10, and Sucrose12.

In one embodiment, a detergent panel for determining the stability and size of a protein is provided. In one aspect, the panel comprises at least two detergents at or above their critical micelle concentrations, and optionally a positive control and a negative control. In one aspect, the detergents are selected from Table 1. In one aspect, the detergents and controls of Table 1 are used. In one aspect, the stock concentrations provided vary with the CMC value of the detergent, and may for example be 2×, 2.5×, 3×, 10×, 50×, and 100×, as disclosed in the Examples.

In one embodiment, all of the test detergents described above are tested or provided in a kit or panel. In another embodiment, other detergents not disclosed herein can be used in the practice of the invention.

DETAILED DESCRIPTION

Abbreviations and Acronyms

Figure 1:
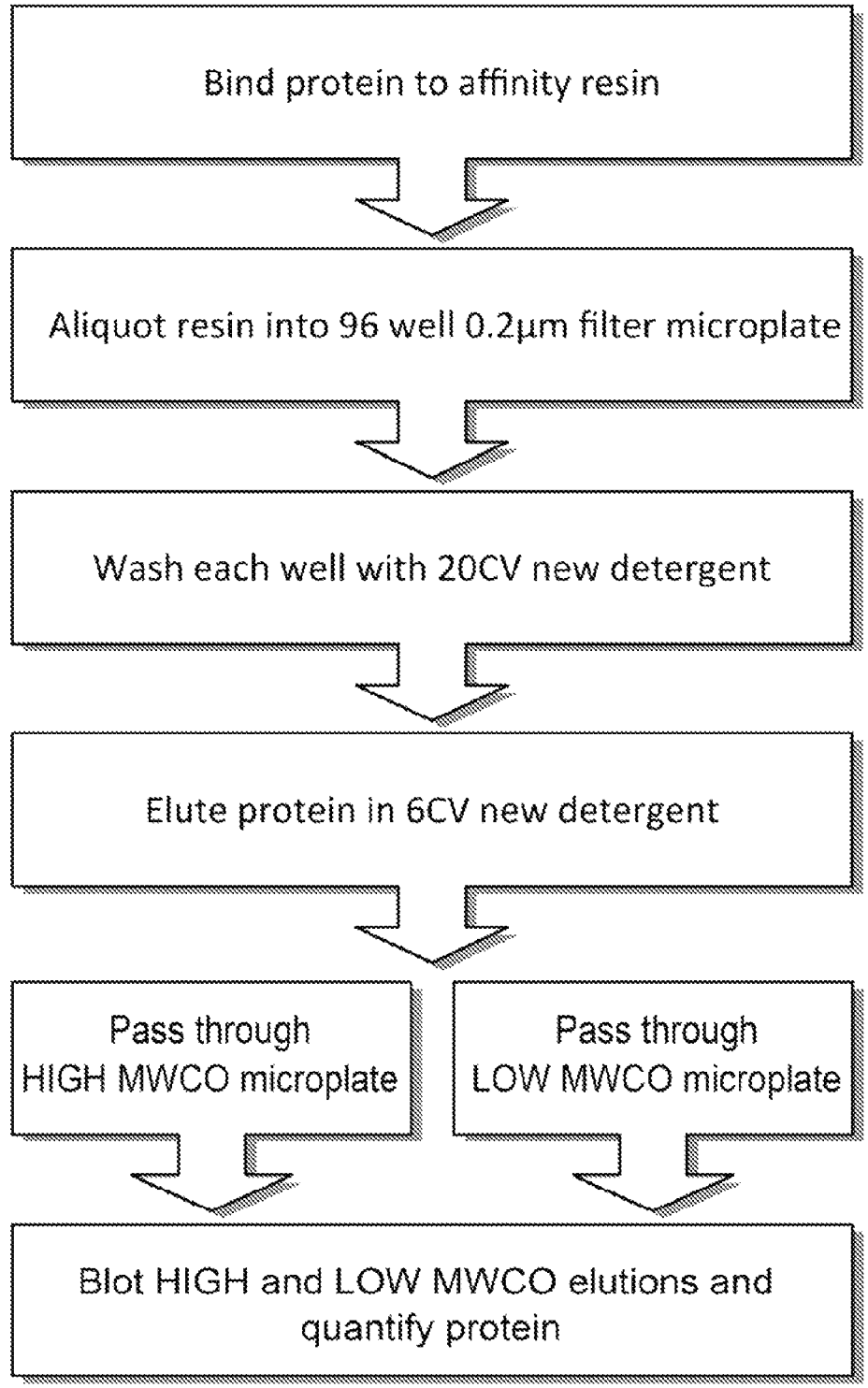
FIG. 1—Flowchart of the detergent stability assay developed herein called Differential Filtration Assay ("DFA"), previously referred to as Prompt Assay of Stability and Size ("PASS"). A generic protocol for performing the assay is presented. Note that the specific compositions for the wash solution of the third step ("Wash each well with 20 CV new detergent") and for the elution solution the fourth step ("Elute protein in 6 CV new detergent") are described in the Materials and Methods section under "Detergent stability assay".

AqpZ—Aquaporin Z
$B_{22}$—second virial coefficient
CMC—critical micelle concentration
CV—column volume
DF—differential filtration
DFA—differential filtration assay (also see PASS)
DM—n-decyl-β-D-maltopyranoside
DTT—dithiothreitol
FID—free interface diffusion
FSEC—fluorescence-detection size-exclusion chromatography
GHP—GH polypro hydrophobic polypropylene
IMAC—immobilized metal affinity chromatography
LDAO—n-dodecyl-N,N-dimethylamine-N-oxide
min—minute(s)
MW—molecular weight
MWCO—molecular weight cutoff
OG—n-octyl-β-D-glucoside
NMR—nuclear magnetic resonance spectroscopy
Membrane Protein Detergent Stability Screen, also referred to as the Prompt Assay of Stability and Size (PASS)—PASS
PASS—prompt assay of stability and size (also see DFA)
MPEG—polyethylene glycol monomethylether
PDC—protein detergent complex
PEG—polyethylene glycol
PES—polyethersulfone
SBS—Society for Biomolecular Sciences
SEC—Size Exclusion Chromatography
SEC-M—Size Exclusion Chromatography-Mimetic
TCA—trichloroacetic acid
TCEP—tris(2-carboxyethyl) phosphine hydrochloride

DEFINITIONS

In describing and claiming the invention, the following terminology will be used in accordance with the definitions set forth below. Unless defined otherwise, all technical and scientific terms used herein have the commonly understood meaning by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

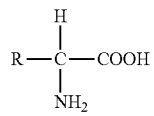

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

A "compound," as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

A "chamber", as used herein, refers to something to which a solution can be added, such as a tube or well of a multiwell plate, etc.

By the phrase "contacting a sample of a protein with at least one formulation" means that if more than one formulation is tested that the sample of the protein is either tested as an aliquot from the sample or that separate samples of the protein are prepared and used.

The use of the word "detect" and its grammatical variants is meant to refer to measurement of the species without quantification. The terms "detect" and "identify" are used interchangeably herein.

An "effective amount of an affinity resin", as used herein, is an amount of resin needed to bind a protein in the detergent.

A "filter plate" as used herein, refers to a plate or other such device, where the bottom or an aspect of the well(s) or chamber(s) comprises a filter. For example, the plate can be a multiwell plate where the bottom of each well is a filter. The practice of the invention is not limited to the use of just those filter plates described herein.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

A "formulation sample" or "sample of a formulation" means an aliquot of the designated formulation. When referenced in a kit, the aliquot is enough to perform at least one experiment for a protein sample. In one aspect, the formulation sample may be in a quantity such that multiple experiments can be performed. A kit may also contain multiple samples of each formulation.

As used herein, the term "high" or "high plate" refers to a molecular weight cut-off plate which has a higher molecular weight cut-off than the companion low molecular weight cut-off plate with which it is paired for the size determination steps of the invention.

As used herein, the term "low" or "low plate" refers to a molecular weight cut-off plate which has a lower molecular weight cut-off than the companion high molecular weight cut-off plate with which it is paired for the size determination steps of the invention.

As used herein, an "instructional material" includes a publication, a recording, a diagram, or any other medium of expression which can be used to communicate the usefulness of the formulations and methods of the invention in the kit. The instructional material of the kit of the invention may, for example, be affixed to a container which contains the identified formulations of invention or be shipped together with a container which contains the identified compound. Alternatively, the instructional material may be shipped separately from the container with the intention that the instructional material and the formulations be used cooperatively by the recipient.

By the term "optionally centrifuging" a filter plate, well, or chamber is meant centrifuging it to enhance filtration.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The terms "solid support", "surface" and "substrate" are used interchangeably and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates when a sample is processed or subjected to purification or extraction procedures before a marker of interest is measured.

Embodiments

Structural studies on integral membrane proteins are routinely performed on protein-detergent complexes (PDCs) consisting of purified protein solubilized in a particular detergent. Of all of the membrane proteins crystal structures solved to date, a subset of only four detergents has been used in over half of these structures.

Unfortunately, many membrane proteins are not well-behaved in these four detergents and/or fail to yield well-diffracting crystals. Identification of detergents that maintain the solubility and stability of a membrane protein is a critical step, and can be a lengthy and "protein-expensive" process. There is an unmet need for compositions and methods useful for screening multiple detergents and determining those best suitable for proteins to obtain well-diffracting crystals. The present application discloses an assay that characterizes the stability and size of membrane proteins exchanged into a panel of 94 commercially available and chemically diverse detergents. DFA, utilizing a set of SBS-format filtered microplates, requires sub-milligram quantities of purified protein, small quantities of detergents and other reagents, and is performed in its entirety in several hours.

When membrane proteins are removed from their lipid-rich, hydrophobic environment into an aqueous environment, surfactants/detergents are typically used to maintain their structure and activity by mimicking their native environment.

The current methods employed by others in the field include:

1) Traditional Gel Filtration Chromatography—inject a purified membrane protein onto a column equilibrated into a test detergent and evaluate the "goodness" of the elution chromatogram. This method is time consuming, material expensive, and is not a detergent exchange but a dilution method.

2) Generic Mobile Phase Gel Filtration Chromatography—this is the same as the previous method except the protein is first diluted into the test detergent and then injected onto a column equilibrated in a known "good" detergent. The premise is that if the new detergent destabilizes the protein, the good detergent will not rescue it and produce a good chromatogram. We have found in our lab that this is not true for all cases so we do not subscribe to this method. This method is quicker than traditional gel filtration in that there is no column equilibration step but it still suffers from the other shortcomings.

3) $Abs_{320}$ nm/$Abs_{280}$ nm Ratio—the protein is concentrated and then diluted 10-100 fold into a new detergent. An increase in the $Abs_{320}$ value is indicative of precipitated protein and thus an incompatible detergent. This method has a high throughput capability but the concentration step required to give a meaningful $Abs_{280}$ value after dilution allows for the original detergent to be concentrated as well during the concentration step. This could prevent the original detergent to not be diluted below its CMC value and thus protect the protein from the new detergent, resulting in a false positive.

4) Ultracentrifugation/SDS PAGE—the protein is diluted and concentrated in a new detergent several times using a centripetal concentrator. An aliquot of this sample is taken for SDS-PAGE while the rest is spun in an ultracentrifuge to pellet any precipitated protein. Another SDS-PAGE sample is made from the supernate of the ultracentrifugation run and both are run on an SDS-PAGE protein gel. Differences in band intensity before and after the ultracentrifugation step are indicative of an incompatible detergent. This method suffers from the same shortcoming as the previous method due to the centripetal concentration step. Also, the ultracentrifugation step is not amenable to high throughput.

However, the method of the present invention overcomes the speed limitations of other methods by simultaneously examining multiple samples, in one aspect 94 samples, in parallel using high throughput methods, small amounts of materials (both protein and detergents) are required, and this method is an exchange method so there is no worry about the original detergent not being diluted below its CMC value.

In order to obtain sizing information on the protein: detergent complex (PDC) without using gel filtration chromatography we implemented the use of the MWCO filtered microplates to create a Size Exclusion Chromatography Mimetic, or SEC-M, also referred to as DF. Utilizing two different molecular weight cut-offs, such as 300 kDa and 100 kDa plates, one can obtain rudimentary sizing information of the PDC in a fraction of the time it would take to run all the samples over gel filtration.

The present invention provides compositions and methods useful for quickly determining the stability and size of a protein by using multiple detergents and methods for applying detergent solutions comprising a protein to a series filters with varied molecular weight cut-offs, and allows for the selection of an appropriate detergent for use with the protein. In one aspect, the protein is a membrane protein.

In one embodiment, the present invention provides a first step, where a buffer exchange technique is used to exchange low quantities of purified protein into the detergents being used in the screening panel of multiple detergents. In one aspect, the technique involves binding the protein to an affinity resin, extensively washing with a new detergent, and then eluting from the chamber or well in the new detergent. Optionally a column could be used and optionally the filtration processes can be enhanced by centrifugation of the well, chamber, or plate being used. In another aspect, filtration can be enhance or speeded up by vacuum. In parallel, aliquots of the eluates are passed through at least two different molecular weight cut-off filters (Low and High) and the amount of protein in the filtrates are measured. In one aspect, the molecular weight cut-offs are about 100 kDa (Low) and about 300 kDa (High). One of skill in the art will appreciate that the terms Low and High are relative and that the two molecular weight cut-off filter sizes described can be modified according to the protein being studied or to other conditions that may effect the flow through.

One of skill in the art will appreciate that the practice of the invention is not limited to the specific devices described herein for filtration.

In one aspect, the amount of protein is measured by dot blot analysis or a rapid Western-blot protocol. Methods are provided herein for measuring and quantifying the dots or Western blots, such as by scanning with an infrared imaging system to determine spot intensities, followed by software analysis, normalization, and graphing. One of ordinary skill in the art will appreciate that other methods may also be used to detect and quantify protein amounts.

In one aspect, the Differential Filtration Assay is performed using at least one 96-well SBS format filter plate.

In one aspect, about 1000 micrograms or less of a protein of interest is needed to perform the Differential Filtration Assay. In another aspect, about 500 micrograms or less is needed. In a further aspect, about 400 micrograms or less is needed. In yet another aspect, about 200 micrograms or less is needed. In a further aspect, about 50 micrograms or less is needed.

In one embodiment, the entire assay is performed in less than two hours. In one aspect, the assay is performed in less than one hour.

In one embodiment, the concentration used of a second detergent is its critical micelle concentration.

Other detergents not described herein can also be used in the assay, either as additional detergents or to substitute for a described detergent.

One important aspect of the present invention is use of detergent exchange, instead of detergent dilution.

In one embodiment, the present invention provides the use of at least two filter plates with different molecular-weight cutoffs (MWCO) to serve as a proxy for gel filtration (size-exclusion) chromatography. As such, it is a novel method for detergent (or any other buffer component) exchange. In one aspect, the present invention provides a novel detergent panel, specifically with respect to the selection of detergents and/or their concentrations. Commercial detergent stock solutions are sold as a fixed percentage (typically 10% weight/volume), while the detergent concentrations in the panel of the present invention are a function of the critical micelle concentration (CMC) of the detergent. In one embodiment, the present invention provides for the use of molecular weight cut off determinations coupled with screening with a panel of detergents.

Non-Detergent Buffer Exchange for Proteins

The disclosure describes the use of DFA technology, previously referred to as PASS, for screening the stability and size of integral membrane proteins as a function of detergent. The 96-well SBS format plates, including those of low and high molecular weight cut-off that comprise the technology called DF (previously referred to as "size-exclusion chromatography mimesis" or "SEC-M"), are coupled with a "composition and concentration" formulated panel of 94 detergents to enable the rapid and "protein-efficient" screening of behavior of a purified protein against this set of detergents. One of ordinary skill will realize that more detergents can be tested by using more plates or plates with more wells or chambers. A further embodiment of DF is its use in multiple well formats, including, but not limited to, 96, 384, and 1536 well plates, for screening any and all buffer components required to maintain stability of proteins. These include, but are not limited to, pH; ionic strength; osmolyte; reductant; specific chemical, element, ion, cofactor, ligand, substrate, nucleic acid or other factor; and other macromolecular components such as proteins.

Use of DFA to Characterize Functional Stability of Membrane (or Other) Proteins

The proof-of-concept and initial demonstration of utility involved the use of recombinant membrane proteins containing poly-histidine affinity tags, and the subsequent immobilization of these proteins on IMAC (immobilized metal-affinity chromatography) resin for use in the assay. Of course, any affinity-based immobilization can also be utilized, such as other exogenous purification tags added to aid in protein purification (including, but not limited to, maltose-binding protein (MBP), glutathione-S-transferase (GST), FLAG, S-tag, strep-tag, chitin-binding domain). All of these exogenously-added tags are independent of the actual function of the protein. However, by use of affinity matrices specific to a given protein's function, this function can be readily characterized in DFA. For example, purified protein (such as a G-protein coupled receptor [GPCR]) can be bound to a ligand-affinity matrix, where the matrix consists of a high-affinity ligand attached to the solid support. The, detergent exchange is performed, using the 94-detergent panel. If a detergent eliminates ligand binding, the protein will be eluted during the exchange step, thus being removed from the resin before elution. The assay is performed in the same way as initially described, but in order to be seen after the DF step, the protein must possess the proper stability, size, and functional integrity in order to be observed.

Use of Affinity-Immobilized Protein and DF for Compound Screening

The purified protein (for example, a GPCR) is bound to a ligand-affinity resin. A compound (or set of pooled compounds) is added to each sample in the plate. If the compound is of comparable or higher affinity to the ligand on the ligand-affinity resin, some fraction of the receptor will be eluted. The amount of eluted receptor is then detected, with the fraction of receptor eluting being related to both the affinity of the compound(s) added, and the ability of the compounds to compete for the same binding site as that used by the ligand on the affinity resin.

EXAMPLES

A description of examples of the invention follows. Use of the invention is not limited to these applications. In one embodiment, the invention consists of two parts, the detergent panel and the DF. Both of these are described below along with a protocol to carry out the assay.

Disclosed herein is a microplate-based detergent screening assay called DFA (previously called PASS, see FIG. 1). A standard buffer exchange technique, successfully implemented in screening detergents suitable for extracting proteins from their membrane environment [10; 11; 12], is used to exchange microgram quantities of purified membrane protein into each of the detergents of our 94 detergent panel (Table 1).

Table 1 summarizes the Detergent screen. The components in the detergent plate are shown along with their locations in the plate and concentrations used. The values in parentheses in the [Det] column are the CMC values for each detergent. Detergents in bold were purchased from Avanti Polar Lipids, italics from Bachem, underlined from EMD Biosciences, and all others from Anatrace. Detergents A3 through C9 are zwitterionic while C10 through H12 are nonionic detergents.

TABLE 1

Detergent Screen

| Well | Abbrev. | Name | [Det] mM |
|---|---|---|---|
| A1 | | No detergent (−control) | |
| A2 | | Empty well for current detergent (+control) | |
| A3 | Z3-12 | ZWITTERGENT ® 3-12 | 8.4 (2.8) |
| A4 | Z3-14 | ZWITTERGENT ® 3-14 | 10 (0.2) |
| A5 | DMG | n-Decyl-N,N-dimethylglycine | 38 (19) |
| A6 | DOMG | n-Dodecyl-N,N-dimethylglycine | 4.5 (1.5) |
| A7 | DAO | n-Decyl-N,N-dimethylamine-N-oxide | 21 (10.5) |
| A8 | UDAO | n-Undecyl-N,N,-dimethylamine-N-oxide | 9.6 (3.2) |
| A9 | LDAO | n-Dodecyl-N,N-dimethylamine-N-oxide | 3 (1) |
| A10 | C-DDFOS | C-DODECAFOS ™ | 44 (22) |
| A11 | CF-4 | CYCLOFOS ™-4 | 28 (14) |
| A12 | CF-5 | CYCLOFOS ™-5 | 13.5 (4.5) |
| B1 | CF-6 | CYCLOFOS ™-6 | 8.04 (2.68) |
| B2 | CF-7 | CYCLOFOS ™-7 | 6.2 (0.62) |
| B3 | FC-10 | FOS-CHOLINE ®-10 | 22 (11) |
| B4 | FC-11 | FOS-CHOLINE ®-11 | 5.55 (1.85) |
| B5 | FC-12 | FOS-CHOLINE ®-12 | 4.5 (1.5) |
| B6 | FC-13 | FOS-CHOLINE ®-13 | 7.5 (0.75) |
| B7 | FC-14 | FOS-CHOLINE ®-14 | 6 (0.12) |
| B8 | FC-I11 | FOS-CHOLINE ®-ISO-11 | 53.2 (26.6) |
| B9 | FC-I11-6U | FOS-CHOLINE ®-ISO-11-6U | 51.6 (25.8) |
| B10 | FC-I9 | FOS-CHOLINE ®-ISO-9 | 64 (32) |
| B11 | FC-U10-11 | FOS-CHOLINE ®-UNSAT-11-10 | 15.5 (6.2) |
| B12 | DHPC | 1,2-Diheptanoyl-sn-glycero-3-phosphocholine | 4.2 (1.4) |
| C1 | LPC-10 | LysoPC-10 | 20 (8) |
| C2 | LPC-12 | LysoPC-12 | 7 (0.7) |
| C3 | FOSFEN-9 | FOSFEN ™-9 | 4.05 (1.35) |
| C4 | CHAPS | CHAPS | 20 (8) |
| C5 | CHAPSO | CHAPSO | 20 (8) |
| C6 | DDMAU | n-Dodecyl-N,N-(dimethylammonio)undecanoate | 6.5 (0.13) |
| C7 | DDMAB | n-Dodecyl-N,N-(dimethylammonio)butyrate | 12.9 (4.3) |
| C8 | LAPAO | LAPAO | 4.8 (1.6) |
| C9 | TRIPAO | TRIPAO | 13.5 (4.5) |
| C10 | T-20 | TWEEN ® 20 | 5.9 (0.059) |
| C11 | BRIJ-35 | BRIJ ® 35 | 9.1 (0.091) |
| C12 | TX-100 | TRITON ® X-100 | 11.5 (0.23) |
| D1 | TX-114 | TRITON ® X-114 | 10 (0.2) |
| D2 | TX-305 | TRITON ® X-305 | 6.5 (0.65) |
| D3 | TX-405 | TRITON ® X-405 | 8.1 (0.81) |
| D4 | NID-P40 | [Octylphenoxy]polyethoxyethanol | 15 (0.3) |
| D5 | APO8 | Dimethyloctylphosphine oxide | 80 (40) |
| D6 | APO9 | Dimethylnonylphosphineoxide | 20 (10) |
| D7 | APO10 | Dimethyldecylphosphine oxide | 13.98 (4.66) |
| D8 | APO11 | Dimethylundecylphosphineoxide | 3.6 (1.2) |
| D9 | APO12 | Dimethyldodecylphosphineoxide | 5.7 (0.57) |
| D10 | C6E3 | *Triethylene glycol monohexyl ether* | 46 (23) |
| D11 | C6E4 | *Tetraethylene glycol monohexyl ether* | 60 (30) |
| D12 | C6E5 | *Pentaethylene glycol monohexyl ether* | 74 (37) |
| E1 | C7E5 | *Pentaethylene glycol monoheptyl ether* | 42 (21) |
| E2 | C8E4 | Tetraethylene glycol monooctyl ether | 20 (8) |
| E3 | C8E5 | Pentaethylene glycol monooctyl ether | 17.75 (7.1) |
| E4 | C8E6 | Hexaethylene glycol monooctyl ether | 25 (10) |
| E5 | C10E5 | Pentaethylene glycol monodecyl ether | 8.1 (0.81) |
| E6 | C10E6 | Hexaethylene glycol monodecyl ether | 9 (0.9) |
| E7 | C10E9 | Polyoxyethylene(9)decyl ether | 3.9 (1.3) |
| E8 | C12E8 | Octaethylene glycol monododecyl ether | 9 (0.09) |
| E9 | C12E9 | Polyoxyethylene(9)dodecyl ether | 5 (0.05) |
| E10 | C12E10 | Polyoxyethylene(10)dodecyl ether | 10 (0.2) |
| E11 | C13E8 | Polyoxyethylene(8)tridecyl ether | 10 (0.1) |
| E12 | CHAP | Big CHAP | 8.7 (2.9) |
| F1 | CHAP-D | Big CHAP, deoxy | 4.2 (1.4) |
| F2 | OHES | *Octyl-2-hydroxyethyl-sulfoxide* | 48.4 (24.2) |
| F3 | RDHPOS | *Rac-2,3-dihydroxypropyloctylsulfoxide* | 48.4 (24.2) |
| F4 | GX-100 | Genapol ®X-100 | 7.5 (0.15) |
| F5 | HTG | n-Heptyl-β-D-thioglucopyranoside | 58 (29) |
| F6 | OG | n-Octyl-β-D-glucopyranoside | 36 (18) |
| F7 | NG | n-Nonyl-β-D-glucopyranoside | 16.25 (6.5) |
| F8 | CYGLU-3 | CYGLU ®-3 | 56 (28) |
| F9 | HECAMEG | HECAMEG | 39 (19.5) |
| F10 | HEGA-9 | Hega ®-9 | 78 (39) |
| F11 | C-HEGA-10 | C-Hega ®-10 | 70 (35) |
| F12 | C-HEGA-11 | C-Hega ®-11 | 23 (11.5) |
| G1 | CYMAL-3 | CYMAL ®-3 | 60 (30) |
| G2 | CYMAL-4 | CYMAL ®-4 | 19 (7.6) |
| G3 | CYMAL-5 | CYMAC ®-5 | 7.2 (2.4) |
| G4 | CYMAL-6 | CYMAL ®-6 | 5.6 (0.56) |

TABLE 1-continued

Detergent Screen

| Well | Abbrev. | Name | [Det] mM | |
|---|---|---|---|---|
| G5 | CYMAL-7 | CYMAL ®-7 | 9.5 | (0.19) |
| G6 | DMHM | 2,6-Dimethyl-4-heptyl-β-D-maltoside | 55 | (27.5) |
| G7 | OM | n-Octyl-β-D-maltopyranoside | 39 | (19.5) |
| G8 | NM | n-Nonyl-β-D-maltopyranoside | 15 | (6) |
| G9 | DαM | n-Decyl-α-D-maltopyranoside | 4.8 | (1.6) |
| G10 | DM | n-Decyl-β-D-maltopyranoside | 5.4 | (1.8) |
| G11 | UDαM | n-Undecyl-α-D-maltopyranoside | 5.8 | (0.58) |
| G12 | UDM | n-Undecyl-β-D-maltopyranoside | 5.9 | (0.59) |
| H1 | ωUDM | ω-Undecylenyl-β-D-maltopyranoside | 3.6 | (1.2) |
| H2 | DDαM | n-Dodecyl-α-D-maltopyranoside | 7.5 | (0.15) |
| H3 | DDM | n-Dodecyl-β-D-maltopyranoside | 8.5 | (0.17) |
| H4 | TDM | n-Tridecyl-β-D-maltopyranoside | 1.5 | (0.03) |
| H5 | OTM | n-Octyl-β-D-thiomaltopyranoside | 21.25 | (8.5) |
| H6 | NTM | n-Nonyl-β-D-thiomaltopyranoside | 9.6 | (3.2) |
| H7 | DTM | n-Decyl-β-D-thiomaltopyranoside | 9 | (0.9) |
| H8 | UDTM | n-Undecyl-β-D-thiomaltopyranoside | 10.5 | (0.21) |
| H9 | DDTM | n-Dodecyl-β-D-thiomaltopyranoside | 5 | (0.05) |
| H10 | S-8 | Sucrose8 | 48.8 | (24.4) |
| H11 | S-10 | Sucrose10 | 7.5 | (2.5) |
| H12 | S-12 | Sucrose12 | 15 | (0.3) |

Table 2 provides a summary of the common or brand names for the detergents used and their chemical names.

TABLE 2

Detergent Chemical Names

| Name | Chemical Name |
|---|---|
| ZWITTERGENT ® 3-12 | n-Dodecyl-N,N-dimethyl-3-ammonio-1-propanesulfonate |
| ZWITTERGENT ® 3-14 | n-Tetradecyl-N,N-dimethyl-3-ammonio-1-propanesulfonate |
| C-DODECAFOS ™ | Cyclododecyl-1-phosphocholine |
| CYCLOFOS ™-4 | 4-Cyclohexyl-1-butylphosphocholine |
| CYCLOFOS ™-5 | 5-Cyclohexyl-1-pentylphosphocholine |
| CYCLOFOS ™-6 | 6-Cyclohexyl-1-hexylphosphocholine |
| CYCLOFOS ™-7 | 7-Cyclohexyl-1-heptylphosphocholine |
| FOS-CHOLINE ®-10 | n-Decylphosphocholine |
| FOS-CHOLINE ®-11 | n-Undecylphosphocholine |
| FOS-CHOLINE ®-12 | n-Dodecylphosphocholine |
| FOS-CHOLINE ®-13 | n-Tridecylphosphocholine |
| FOS-CHOLINE ®-14 | n-Tetradecylphosphocholine |
| FOS-CHOLINE ®-ISO-11 | 2,8-Dimethyl-5-nonylphosphocholine |
| FOS-CHOLINE ®-ISO-11-6U | Undecyl-6-phosphocholine |
| FOS-CHOLINE ®-ISO-9 | 2,6-Dimethyl-4-heptylphosphocholine |
| FOS-CHOLINE ®-UNSAT-11-10 | 10-Undecylenyl-1-phosphocholine |
| LysoPC-10 | 1-Decanoyl-2-hydroxy-sn-glycero-3-phosphocholine |
| LysoPC-12 | 1-Lauroyl-2-hydroxy-sn-glycero-3-phosphocholine |
| FOSFEN ™-9 | Nonylphenylphosphocholine |
| CHAPS | 3-[(3-Cholamidopropyl)dimethylammonio]-1-propanesulfonate |
| CHAPSO | 3-[(3-Cholamidopropyl)dimethylammonio]-2-hydroxy-1-propanesulfonate |
| LAPAO | 3-Dodecylamido-N,N'-dimethylpropyl amine oxide |
| TRIPAO | 3-(3 Butyl-3-phenylheptanamido)-N,N-dimethylpropan-1-amine oxide |
| TWEEN ® 20 | Polyoxyethylene(20) sorbitane monolaurate |
| BRIJ ® 35 | Polyoxyethylene lauryl ether |
| TRITON ® X-100 | α-[4-(1,1,3,3-Tetramethylbutyl)phenyl]-ω-hydroxy-poly(oxy-1,2-ethanediyl), average MW 647 |
| TRITON ® X-114 | α-[4-(1,1,3,3-Tetramethylbutyl)phenyl]-ω-hydroxy-poly(oxy-1,2-ethanediyl), average MW 536 |
| TRITON ® X-305 | α-[4-(1,1,3,3-Tetramethylbutyl)phenyl]-ω-hydroxy-poly(oxy-1,2-ethanediyl), average MW 1526 |
| TRITON ® X-405 | α-[4-(1,1,3,3-Tetramethylbutyl)phenyl]-ω-hydroxy-poly(oxy-1,2-ethanediyl), average MW 1967 |
| Big CHAP | N,N'-bis-(3-D-Gluconamidopropyl)cholamide |
| Big CHAP, deoxy | N,N'-bis-(3-D-Gluconamidopropyl)deoxycholamide |
| Genapol ® X-100 | Polyoxyethylene (10) Isotridecyl Ether |
| CYGLU ®-3 | 3-Cyclohexyl-1-propyl-β-D-glucoside |
| HECAMEG | Methyl-6-O-(N-heptylcarbamoyl)-α-D-glucopyranoside |
| Hega ®-9 | Nonanoyl-N-hydroxyethylglucamide |
| C-Hega ®-10 | Cyclohexylbutanoyl-N-hydroxyethylglucamide |
| C-Hega ®-11 | Cyclohexylpentanoyl-N-hydroxyethylglucamide |
| CYMAL ®-3 | 3-Cyclohexyl-1-propyl-β-D-maltoside |
| CYMAL ®-4 | 4-Cyclohexyl-1-butyl-β-D-maltoside |
| CYMAL ®-5 | 5-Cyclohexyl-1-pentyl-β-D-maltoside |
| CYMAL ®-6 | 6-Cyclohexyl-1-hexyl-β-D-maltoside |
| CYMAL ®-7 | 7-Cyclohexyl-1-heptyl-β-D-maltoside |
| Sucrose8 | n-Octanoyl-β-D-fructofuranosyl-α-D-glucopyranoside |
| Sucrose10 | α-D-Glucopyranoside, β-D-Fructofuranosyl Monodecanoate |
| Sucrose12 | n-Monododecanoate-α-D-glucopyranoside, β-D-Fructofuranosyl |

This simple technique involves binding the protein to an affinity resin, extensively washing with the new detergent, and finally eluting from the column in the new detergent. In parallel, these eluents are each passed through high and low molecular weight cutoff (MWCO) filter plates. The amounts of protein in the filtrates are measured by a rapid Western-blot protocol. DFA is performed with 96-well SBS format filter plates, for further increasing speed and decreasing reagent and protein costs.

The assay disclosed herein addresses the limitations of the detergent screening methods described above, and provides measures of both stability and rudimentary size information.

Typically, results can be obtained in approximately two hours with only few hundred micrograms of protein required for the assay. Furthermore, DFA can be completely automated if desired. To validate the assay, we present DFA data of two membrane proteins, AqpZ and KcsA. Both of these membrane proteins have been crystallized and their structures initially solved by other laboratories.

For the purpose of this application (and corresponding to a standard empirical definition), we define the stability of a membrane protein in a given detergent to be a quantity that is inversely proportional to the fraction of PDCs that form large particles or aggregates in that specific detergent. If all of the protein forms large particles or aggregates (which would be present in the void volume of a suitable gel filtration column, for example), then we would call that protein sample unstable. If none of the protein forms large particles or aggregates (such that the protein would be seen as one or more sizing peaks in the aforementioned gel filtration column), then we would call that protein sample stable. [Of course, stability, generally a time-dependent property, is not affected solely by detergent.]

Materials and Methods

Detergent Panel—

All chemicals for the detergent panel were purchased from Anatrace, Avanti Polar Lipids, Bachem, and EMD Biosciences as indicated in Table 1. 2× working stock solutions were made in ultra-pure water, dispensed into 96-well plates, heat sealed with foil tape and frozen at −20° C. until needed.

MWCO Filtered Microplate Assessment—

Stock solutions of each gel filtration MW standard (Sigma and GE Healthcare) at 2-5 mg/ml were made in PBS buffer. 30 µl of each stock solution was added to a 0.2 µm filter plate (Part #5045, Pall Corp.) and 100 kDa and 300 kDa MWCO filter plates (#T-3180-14 and #T-3180-21 ISC Bioexpress, or #CMR1411 and #CMR1493-1 Seahorse Labware) and spun at 2000×g for 2 min. We emphasize that these values of 100 kDa and 300 kDa MWCO are the names given to these plates by the manufacturer. As will be shown, the actual MWCOs measured are different. We will henceforth use the nomenclature "low" and "high" for the 100 kDa and 300 kDa plates, respectively, to indicate the relative difference in the molecular weight cut-offs of the filters. The filter plate flow through along with samples of the original stock solutions were transferred to a UV transparent 384-well plate and $Abs_{280\ nm}$ was measured on a Molecular Devices SpectraMax 384 Plus spectrophotomer with PathCheck (i.e., 1 cm path length correction) active. The percent difference between the stocks and eluate absorbance values were used to calculate the flow through percent for each standard through each filter type. The errors are the standard deviations obtained from measuring three separate samples in each filtered microplate.

Purification of AqpZ and KcsA—

Both $(His)_6$-AqpZ (cys-free) and $(His)_6$-KcsA were overexpressed and purified from *E. coli* by slight modification of published methods [13; 14]. The AqpZ buffer was 20 mM Tris pH 7.4, 500 mM NaCl, 10% glycerol, and 40 mM OG. The KcsA buffer was 20 mM Tris pH 7.4, 150 mM KCl, and 1 mM DDM. Both purifications were only carried out to the first IMAC step with Co-TALON (Clontech) resin and then desalted back into the respective buffers with PD 10 columns (GE Healthcare). KcsA was further processed by digestion with chymotrypsin (Worthington Biochemical Corp.) for 4 hrs at RT with a 1:25 Chymotrypsin:KcsA ratio by mass. The chymotrypsin was removed with immobilized benzamidine (GE Healthcare).

Detergent Stability Assay—

400 µg of AqpZ or KcsA were batch-bound to 1.5 ml of Co-TALON resin (0.27 µg protein/µl resin) along with additional buffer to a final volume of 7.5 ml making a 20% slurry. 50 µl of the protein-bound resin slurry (10 µl resin) was then added to the 0.2 µm filter microplate using a multichannel pipette with the ends of the tips cut to make a wider bore. The resin was pelleted in the microplate by spinning at 2000×g for 2 min at 4° C. The detergent containing wash solutions were prepared from the 2× detergent stock panel and 2× buffer stocks. 3 CV (Column Volumes) of the detergent wash solution was added to each well and the microplate was spun at 2000×g for 2 min at 4° C. to remove the buffer. This washing is repeated until 20 CV of detergent wash buffer had been added. The elution solutions were prepared from the 2× detergent stock panel and 2× elution buffer stocks (2× wash buffer containing 1M imidazole). The detergent exchanged protein was then eluted from the resin in 6 CV of elution solution by spinning the plate at 2000×g for 2 min at 4° C. into a PCR collection plate (Abgene). 25 µl of the eluted protein was then added to the 300 kDa (i.e., high) MWCO filter microplate and 25 µl added to the 100 kDa (i.e., low) MWCO filter plate, the plates spun at 2000×g for 2 min at 4° C. and the eluate collected in a PCR collection plate. The Minifold I 96-well Dot-Blot apparatus (Whatman) was used to blot the elution samples onto 0.2 µm nitrocellulose (Whatman). Due to the spot-broadening effects of some detergents, the protein was precipitated in the blotting apparatus with trichloroacetic acid (TCA) prior to applying the vacuum. 150 µl of 10% TCA was first added to each well of the assembled dot-blot apparatus followed by 10 µl of the eluate from each MWCO filter plate. Vacuum was applied to filter the sample through the nitrocellulose and each well was washed with 20 mM Tris pH 7.4, 500 mM NaCl three to four times. The membranes were quickly washed with ultra-pure water and blocked for 10 min with Odyssey blocking buffer (LI-COR Biosciences). The membranes were probed for 10 min with an IRDye®800CW conjugated anti-6× His Tag antibody (Rockland Immunochemicals) diluted 1:10000 in Western Breeze Primary Antibody Diluent (Invitrogen). The blots were washed with Western Breeze Antibody Wash (Invitrogen) four times for 2 min each and then with ultra-pure water. The blots were scanned on an Odyssey Infrared Imaging System (LI-COR Biosciences) with the intensity adjusted to avoid saturation of the spots. Integrated spot intensities were measured with the Odyssey software and the background for each spot was calculated from the median value of the baseline surrounding the spot. The background-corrected integrated spot intensities were then exported to a spreadsheet for normalization and graphing.

Gel Filtration Runs—

Detergent exchanges using larger amounts of protein (12 µg protein/µl resin) for gel filtration were carried out in 0.22 µm filter spin columns (Millipore) and a table top centrifuge using the same detergent exchange protocol above except the protein was eluted in only 3 CV and 150 mM EDTA was substituted for imidazole in the elution buffer in order to avoid imidazole fluorescence during gel filtration. 10 µl eluted protein was loaded onto a calibrated Superdex™ 200 5/150 GL "short column" (GE Healthcare) at 0.4 ml/min. The column was equilibrated in the exchange detergent prior to sample injection. The intrinsic protein fluorescence (Ex280 nm/Em335 nm) was monitored using a Hitachi L-2485 fluorescence detector.

Other methods not described herein but which are useful in the practice of the invention are incorporated herein by reference in their entirety, including those International Patent Application Serial No. PCT/US2010/036562 (Wiener et al.; filed May 28, 2010).

Results

Size-Exclusion Chromatography Mimesis (i.e., DF)—

The use of multiple differing molecular weight cutoff (MWCO) filters in parallel permits acquisition of rudimentary size information on PDCs. It is important to note that MWCO filters do not have a single sharp molecular weight cutoff. Instead, a given filter will exclude approximately all particles above a certain size, will pass approximately all particles below a certain size, and will let through some fraction of particles between these two limits. For the purposes of DFA, consider two MWCO filter plates: high and low. The high plate excludes particles of large size and permits some or all of the remaining particles to pass through. The retentate of the high plate will consist solely of these large particles; nearly everything else will be in the filtrate.

The low plate has a lower size-exclusion limit. Therefore, the retentate of the low plate will include all of the retentate present in the high plate plus additional retentate arising from the lower cutoff. Thus, in the absence of experimental error, the fraction of a sample in the filtrate of the low plate will always be less than or equal to the fraction of that sample in the high plate filtrate.

Figure 2:
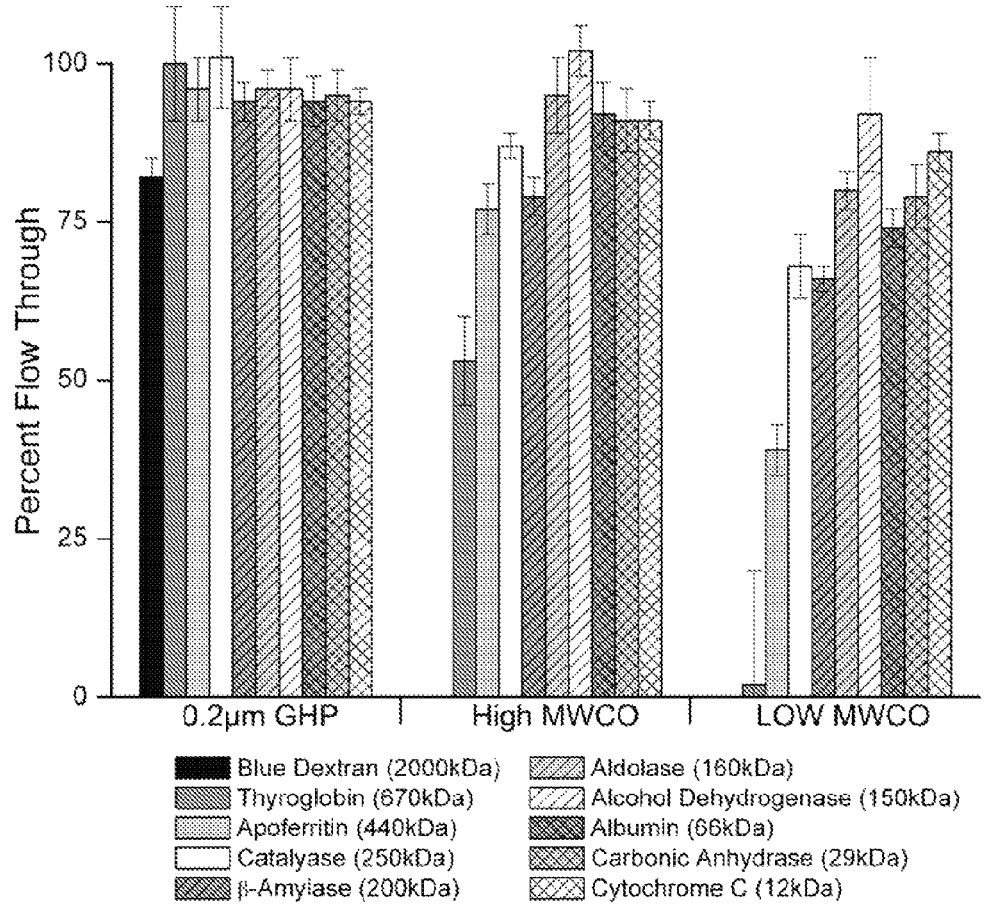
FIG. 2—Graphically depicts filter plate flow through of molecular weight standards. The $Abs_{280}$ nm was measured for each stock solution, and the eluate from each plate in triplicate. The left set of bars represent 0.2 μm GHP, the center set of bars represents the High MWCO (molecular weight cut-off) group, and the right set of bars represents the Low MWCO group. Bars represent Blue Dextran, Thryoglobin, Apoferritin, Catalyase, b-Amylase, Aldolase, Alcohol Dehydrogenase, Albumin, Carbonic Anhydrase, and Cytochrome C. The Ordinate represent Percent Flow Through. The percent difference between the eluate and the stock is presented on the graph. The error bars represent the error propagated from the standard deviation of each triplicate measurement. No passage of blue dextran was observed in either the high or low MWCO filter plates.

During the conception of the detergent screening assay, gel filtration of the eluted samples was planned to be performed using either a generic mobile phase or detergent-specific mobile phase in conjunction with an in-line fluorescence detector to follow intrinsic protein fluorescence of the protein of interest. It became readily apparent that this would not work due to the fluorescence of a large population of the detergents in the panel themselves (data not shown). As an alternative to gel filtration for obtaining sizing information, or at the very least to remove any protein aggregate analogous to that present in the void volume of a gel filtration run, filtration through MWCO PES (polyethersulfone) filters was employed. Because MWCO PES filters are not absolute cut-offs but instead permit a range of particle sizes to pass through their membrane, SBS format MWCO filterplates from several manufactures were evaluated. The size distribution range for each MWCO filterplate was measured using gel filtration MW standards. A sizing microplate was sought that would disallow passage of blue dextran (the 2000 kDa void volume MW standard) and produce a suitable MW distribution for estimating size. A single MWCO filtered microplate was not sufficient to satisfy both criteria because the MW permeability range was too narrow for the low plate and too broad for the high plate. To overcome this deficiency, low and high MWCO microplates were paired together for the assay. The MW distributions of these two MWCO filtered microplates along with the 0.2 μm GHP (GH Polypro, hydrophobic polypropylene) filter plate are shown in FIG. 2.

As expected, the 0.2 μm plate allows passage of all of the gel filtration standards, with equal and complete permeability of all of standards except blue dextran (partially permeable). In contrast, neither the low nor the high plates allow blue dextran to flow through, and thus prevent highly aggregated protein from passing through. With the use of both MWCO microplates, analysis of the high microplate filtrate reports primarily on stability, and the ratio of the low and high plate filtrates reports on size. Thus, MWCO filters are used to mimic sizing data obtained sizing data obtained by gel filtration chromatography. We call this technique DF (previously referred to as "Size-exclusion Chromatography Mimesis" or "SEC-M").

The Detergent Panel—

The assay in its current form utilizes 96-well SBS format microplates. We utilize our 94-detergent panel (Table 1) plus negative and positive positions A1 and A2 of the microplates. The negative control contains detergent-free buffer, which will cause the protein to precipitate on the resin, while the positive control is the current detergent containing buffer. Even though it is highly probable that the current detergent used for a given protein is present in the panel, the working concentrations of the detergent may be different. The chemical (or trademarked names), well locations, abbreviations, working concentrations, and CMC values for each detergent in the panel are shown in Table 1.

All of the detergents were selected for their suitability for membrane protein studies based upon several criteria: 1) commercial availability; 2) moderate or high aqueous solubility; 3) CMC values between 0.03 and 40 mM; and 4) zwitterionic or nonionic headgroups. The detergent panel is first grouped into zwitterionic and nonionic sets, further ordered by chemical class, then by chain length within each chemical class where applicable, and finally by CMC value. This permits the facile recognition of patterns of stability. The detergent stock plate consists of 2× working concentration solutions dispensed and heat sealed into single use microplates, for ease in formulation of the wash and elution buffers. Each detergent's working concentration in the panel varies with respect to its CMC value: 2× (CMC>10 mM); 2.5× (CMC 5-10 mM); 3× (CMC 1-5 mM); 10× (CMC 0.5-1 mM); 50× (CMC 0.1-0.5 mM); 100× (CMC<0.5 mM). The exception is TDM where the working concentration is 50× due to solubility issues. The use of several CMC multiples is necessary due to low-CMC detergents being required at higher concentrations (in terms of their CMC) than high-CMC detergents [5].

Visualization and Quantification of the Elutions—

Figure 3:
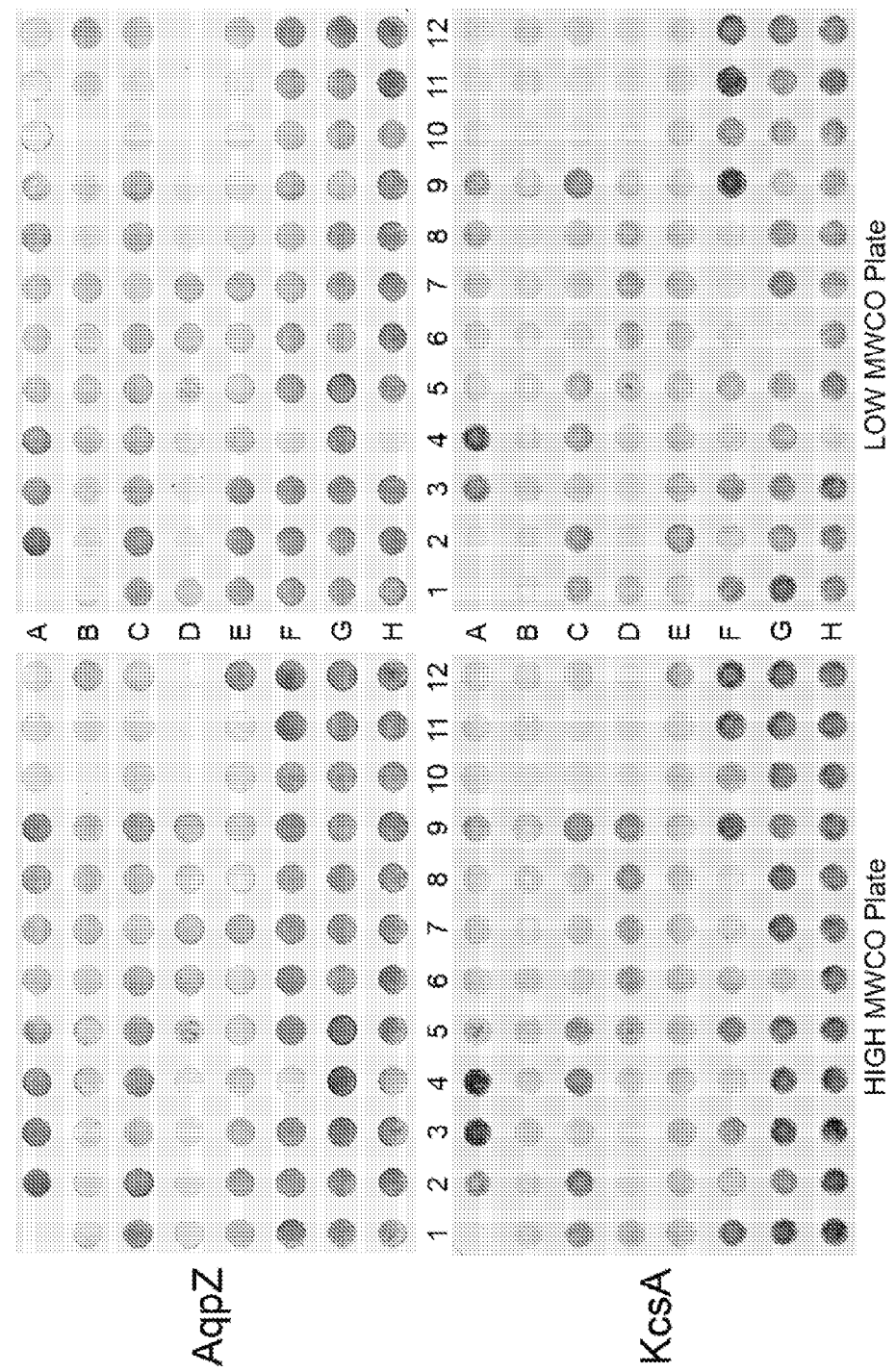
FIG. 3 (FIGS. 3A-3D)—Dot blots of eluted protein after exchange into the new detergent. 10 μl of the elutions from the high and low MWCO plates were spotted on nitrocellulose membrane and visualized by Western blot using an IRDye®800CW conjugated His-tag antibody and a LI-COR Odyssey imaging system. The dot intensities were quantified with median background correction within the Odyssey software. The two left panels represent High MWCO plates (FIGS. 3A and 3C) and the two right panels represent Low MWCO plates (FIGS. 3B and 3D). The two upper plates (FIGS. 3A and 3B) represent AqpZ and the two lower plates (FIGS. 3C and 3D) represent KcsA.

Using a fast Western protocol, the elutions for each MWCO microplate are blotted to a nitrocellulose membrane, visualized using a conjugated primary antibody specific to the affinity tag used, and quantified in approximately one hour. Dot blots of the elutions from the AqpZ and KcsA detergent exchanges are shown in FIG. 3. Quantification of dots on the blots measures the amount of protein eluted from each well. Because the same amount of protein was used in each well and an incompatible detergent will cause a membrane protein to precipitate on the affinity resin, the integrated dot intensity is directly related to the ability of a particular detergent to stabilize a membrane protein relative to the other detergents in the panel. As mentioned in the introduction, the loss of membrane protein stability is assayed by the presence of and amount of irreversible aggregates (large particle formation) as a function of the detergent species that is present in the PDC. The low and high dot blots are quantified and normalized to the highest intensity dot on each respective blot. The ratios of the normalized low to high dot intensities are calculated to indicate the relative size of the PDC; this ratio is inversely proportional to the PDC size, with larger ratio values indicative of a smaller PDC size. The ratio is a better estimate of size than just the low dot intensities alone. The low dot intensities are related to both size and stability, while the low/high ratio accounts for the removal of any aggregated protein retained by the high microplate (and thus also retained by the low microplate).

Figure 4:
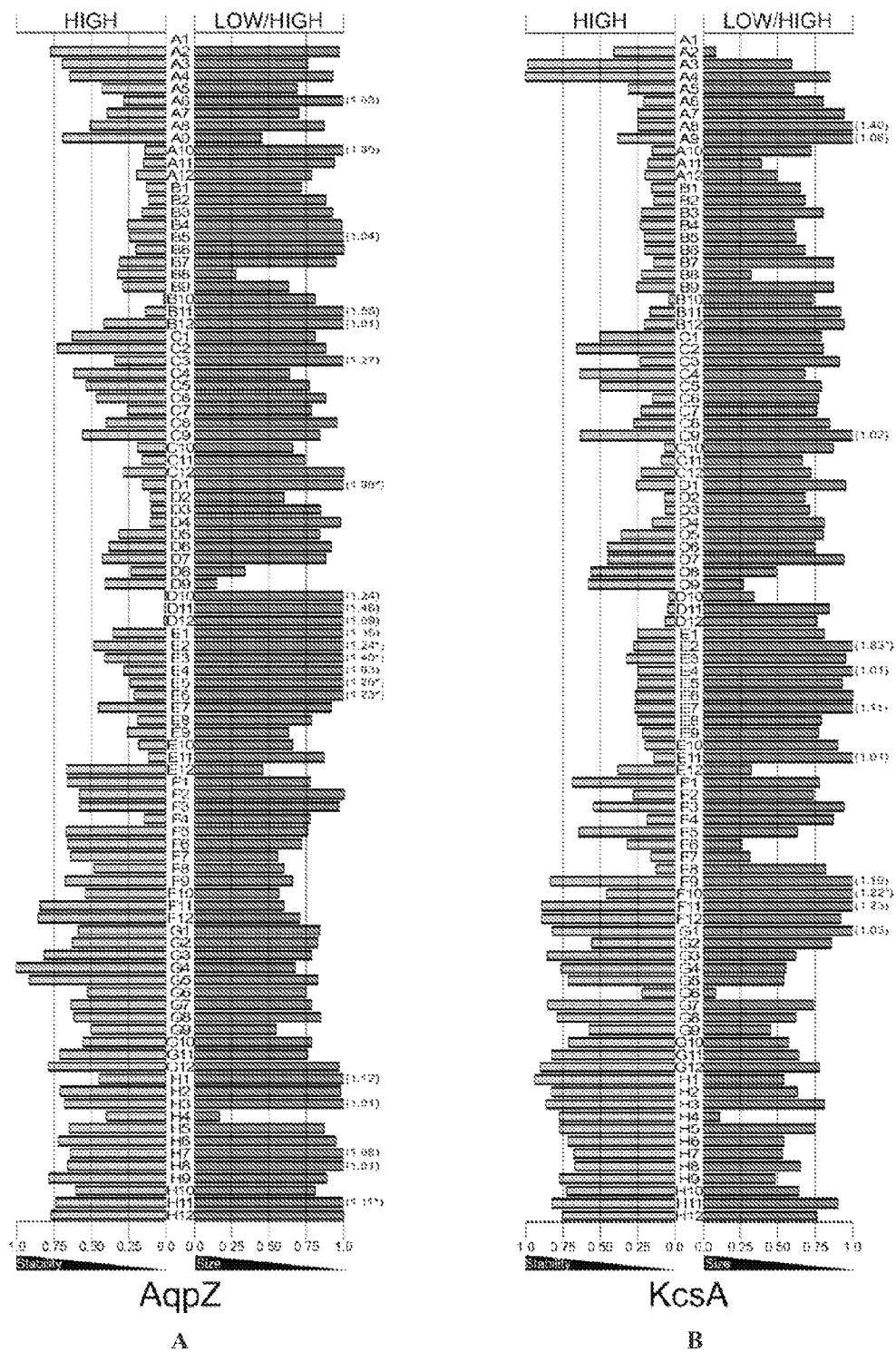
FIG. 4—Stability and relative size bar graphs. The normalized intensities from the high MWCO dot blots are plotted along with the ratio of low:high (low/high) normalized intensities for AqpZ (FIG. 4A) and KcsA (FIG. 4B). The values are grouped into quartiles, indicated by the gridlines. The high intensity is directly proportional to stability while low/high is inversely proportional to the particle size. Non-real ratio values (i.e. low intensity greater than high intensity) are given in parenthesizes. These non-real ratio values are all from high and low intensities within the same quartile rank except those indicated by an asterisk (*).
Figure 5:
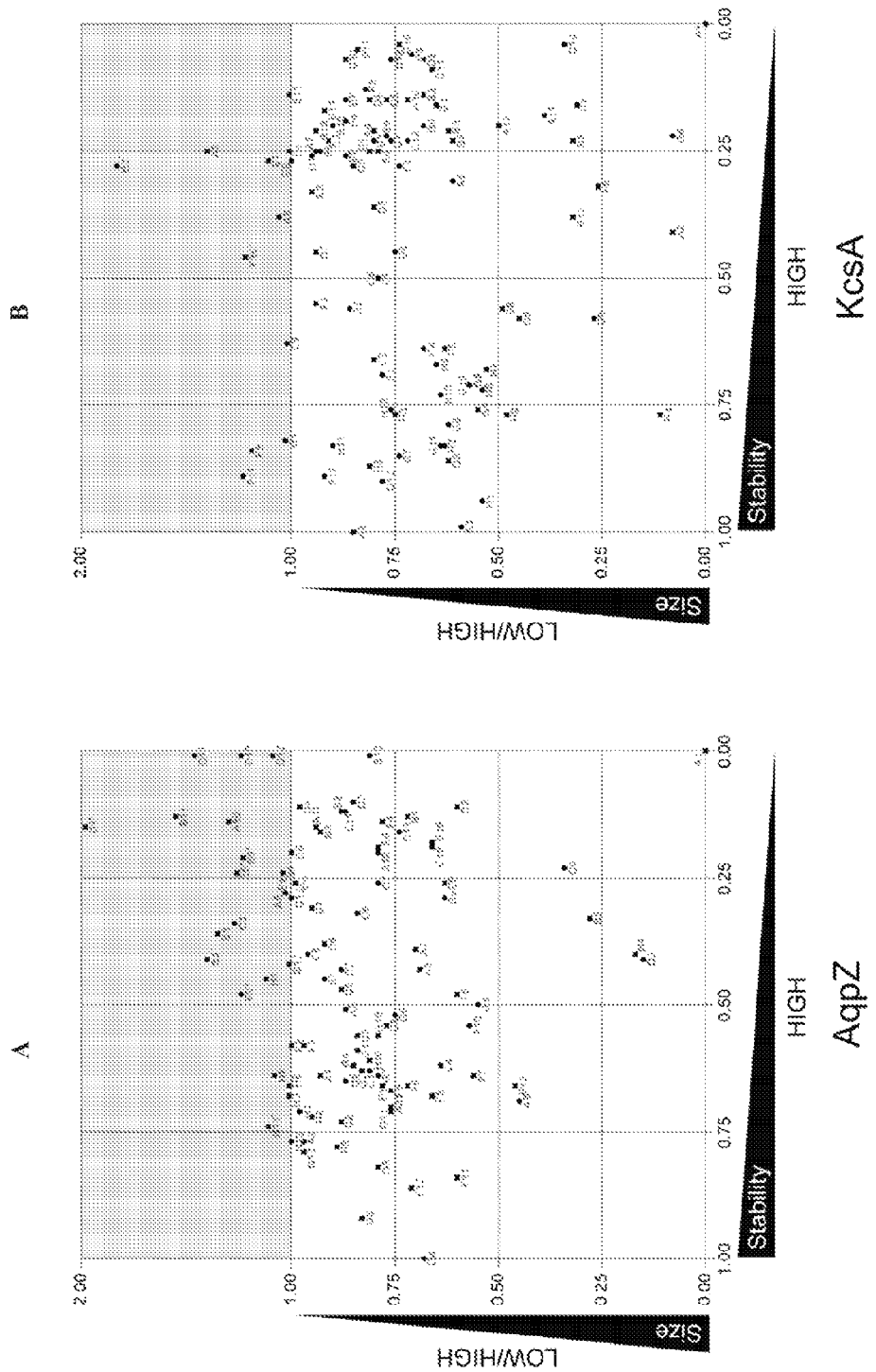
FIG. 5—Quartile grid plot. The normalized intensities from the high MWCO dot blots are plotted on the horizontal axis while the ratios of low:high (low/high) normalized intensities for AqpZ (FIG. 5A) and KcsA (FIG. 5B) are plotted on the vertical axis. The well numbers are shown next to each dot. Non-real ratio values (i.e. low intensity greater than high intensity) are located in the grayed out area of the plot. These non-real ratio values are all from high and low intensities within the same quartile rank except those indicated by an asterisk (*).

FIG. 4 and FIG. 5 demonstrate two representations of the quantified data. FIG. 4, the "audio equalizer representation", presents the data to allow any stability and/or size patterns related to detergent type, chain length, or CMC to be easily elucidated because the detergent panel is organized in that manner. FIG. 5, the "size-stability quad-plot", displays the data to allow quick assessment of PDC size related to stability without any regard for the detergent's physical or chemical properties. The data in both representations are binned into quartiles to help compensate for the inherent error in measuring only one data point. Interestingly, despite AqpZ being a larger tetramer (103 kDa), the KcsA tetramer (55 kDa) possesses a much more variable size dependence as demonstrated by the broader distribution of relative PDC size seen in FIG. 5.

DF Correlates with Gel Filtration—

Figure 6:
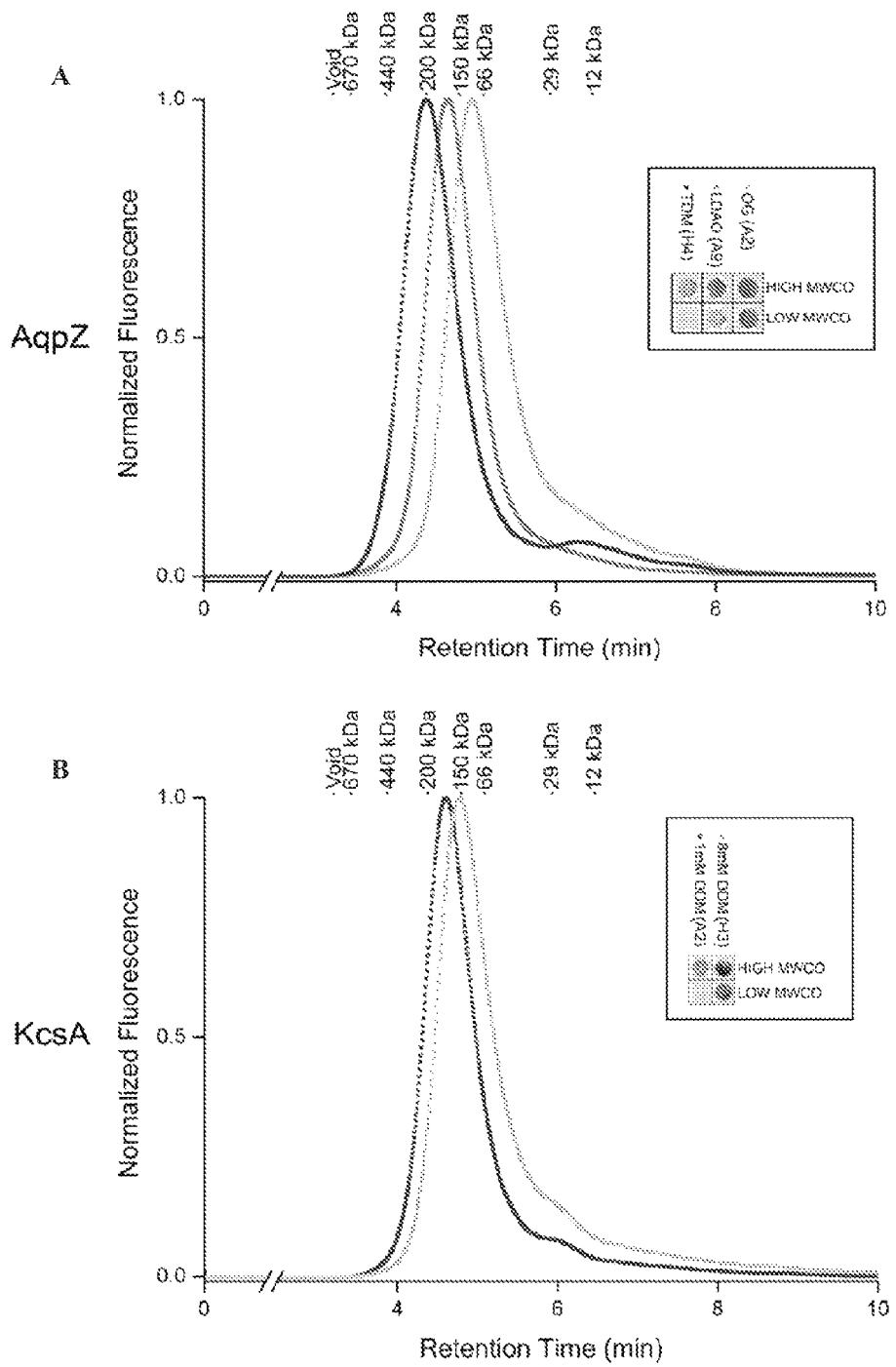
FIG. 6—Low MWCO elution intensity correlates to HPSEC retention time. Larger amounts of AqpZ (FIG. 6A) and KcsA (FIG. 6B) were detergent exchanged using spin columns and then 10 μl injected onto a calibrated Superdex™ 200 5/150 GL gel filtration column equilibrated in the exchanged buffer. The retention times for MW gel filtration standards are shown on each chromatogram. The insets show the dot blot spots for each detergent. The ordinate represents normalized fluorescence and the abscissa represents retention time (in minutes).

In order to further validate the use of the DF technique in the assay, larger scale detergent exchanges were performed on AqpZ and KcsA and samples were run over a calibrated gel filtration column. The retention times of the gel filtration runs were compared to the dot intensities obtained from the two MWCO filter plate elutions. FIG. 6 (top panel) shows three AqpZ gel filtration runs exchanged into TDM, LDAO, and OG along with the corresponding dot blots for those detergents. As predicted from the low elution dot blots, the apparent PDC size order of AqpZ is OG<LDAO<TDM which is inversely proportional to their respective dot blot intensities.

FIG. 6 (bottom panel) demonstrates an interesting phenomenon in which the same detergent at two different concentrations gives two different PDC sizes for KcsA. KcsA in the traditional working concentration of 1 mM DDM is predicted to have a larger PDC size than the same protein in 8.5 mM DDM by both gel filtration and DF. The reason for a higher concentration of detergent reducing the size of the PDC is currently under investigation.

Discussion

We have developed a microplate-based detergent screening assay, the Differential Filtration Assay (DFA). Differential filtration (DF), the simple underlying principle, is that the variation of amounts of macromolecules in filtrates obtained by passage of a macromolecular solution through several different molecular weight cutoff (MWCO) filters provides information on the stability (aggregation) and size of a macromolecular solute as a function of buffer composition. DF rapidly captures significant information that is typically obtained, much more slowly, by SEC. The combination of DF with a specific method for detection and quantitation of filtrates yields a Differential Filtration Assay (DFA). For membrane proteins in PDCs, the detergent of the PDC is often the most significant buffer component; however, DF is equally well-suited for examination of any solution conditions for any macromolecular solute.

Differential Filtration (DF)

The use of multiple differing molecular weight cutoff (MWCO) filters in parallel permits acquisition of rudimentary size information on PDCs. It is important to note that MWCO filters do not have a single sharp molecular weight cutoff. Instead, a given filter will exclude approximately all particles above a certain size, will pass approximately all particles below a certain size, and will let through some fraction of particles between these two limits. For the purposes of DFA, consider two MWCO filter plates: high and low. The high plate excludes particles of large size and permits some or all of the remaining particles to pass through. The retentate of the high plate will consist solely of these large particles; nearly everything else will be in the filtrate. The low plate has a lower size-exclusion limit. Therefore, the retentate of the low plate will include all of the retentate present in the high plate plus additional retentate arising from the lower cutoff. Thus, in the absence of experimental error, the fraction of a sample in the filtrate of the low plate will always be less than or equal to the fraction of that sample in the high plate filtrate.

As an alternative to gel filtration for obtaining sizing information, or at the very least to remove any protein aggregate analogous to that present in the void volume of a gel filtration run, filtration through MWCO PES (polyethersulfone) filters was employed. Since MWCO PES filters are not absolute cutoffs but instead permit a range of particle sizes to pass through their membrane, SBS format MWCO filterplates from several manufactures were evaluated. The size distribution range for each MWCO filterplate was measured using gel filtration MW standards. A sizing microplate was sought that would disallow passage of blue dextran (the 2000 kDa void volume MW standard) and produce a suitable MW distribution for estimating size. We emphasize that a single MWCO filtered microplate was not sufficient to satisfy both criteria since the MW permeability range was too narrow for the low plate and too broad for the high plate. To overcome this deficiency, low and high MWCO microplates were paired together for the assay. With the use of both MWCO microplates, analysis of the high microplate filtrate reports primarily on stability, and the ratio of the low and high plate filtrates reports on size. Thus, analysis of the filtrates of several different MWCO filters captures significant data that is typically obtained by SEC. We call this technique Differential Filtration (DF).

The detergent panel presented here, combined with DFA, provides a robust and rapid means to survey membrane protein stability in a large number of chemically diverse detergents as well as to obtain rudimentary PDC sizing information. While the sizing information obtained from DF does not provide an absolute value for apparent MW, it does provide a coarse filter that allows the results to be binned and ranked for further analysis via traditional SEC as desired. The ability to obtain quickly this sizing and stability information is a significant benefit to this method, especially if the time that would be required to examine all 94 samples with SEC is considered. For the Superdex™ 200 5/150 GL column used in this work, each run is approximately 6 minutes in duration. Use of a generic mobile phase would require approximately 10 hrs, and use of detergent-specific mobile phases would require an additional 44 hrs for column equilibration and pump washing. These time estimates assume no down time and complete automation of the chromatography. Furthermore, many protein samples will aggregate or denature during this time, leading to ambiguous results.

The core technology of the Differential Filtration Assay (DFA) is the use of several different MWCO filters which yield differential filtration (DF) of a macromolecular solute. Detection and quantification of the filtrates, required for application of DF to this specific assay, can be performed by a variety of methods. Factors that influence the choice of detection method include: specific vs. non-specific detection, direct vs. indirect detection, sensitivity, accuracy, precision, time required, and (of course) amount of protein required. Specific detection methods are those that will, essentially, detect only the expressed protein of interest. In this publication, we performed a rapid Western blot protocol which utilized a fluorescent primary antibody to the poly-histidine affinity tag. Antibody-based methods are highly specific, and indirect. A benefit of this high specificity is the ability to perform DFA on less highly-purified samples. However, measurement of antibody binding to quantitate antigen, an indirect method, can introduce significant error, especially if the measurement is performed only once (illustrated by the analysis of error that we have presented here). While error can be decreased by performing multiple measurements of each sample-buffer condition, this increases the time, cost, and amount of protein required to perform the assay. A detection method, that is specific and direct, is measurement of the fluorescence of a small-molecule fluorophore (such as FlAsH) attached to a genetically-encoded binding site of the recombinant protein, or of a fluorescent protein (such as GFP) made as a fusion protein with the target. These are also direct detection methods, as the protein itself is detected. Non-specific direct detection methods are those which detect total amount of protein in the filtrate. These include Lowry and BCA assays, as well as non-specific fluorescent labeling of proteins (such as by amine-reactive fluorophores). A likely advantage of direct fluorescent methods, whether specific or non-specific, is that the high and low MWCO filtrates can go directly into fluorescence microplates for direct reading in a fluorescence plate reader.

With structural biology methodologies moving towards performing experiments on smaller scales with smaller amounts of material (especially important for difficult research problems with limited and/or expensive reagents), the development and use of high throughput methodologies have increased. We present here a true high throughput membrane protein detergent screening assay that can be completed in approximately two hours with microgram amounts of protein and microliter volumes of reagents. DFA helps to overcome the barrier of low protein yields which are unfortunately typical for membrane proteins, especially when using more complex and/or higher order expression systems (e.g. eukaryotic). The assay as presented here used 400 μg of protein to obtain stability and PDC sizing information on 94 different detergents from our panel. This amount of protein is not the absolute minimum amount required to perform the assay. DFA could be conducted with 10-50 μg of protein (or even less) if more sensitive detection of the low and high MWCO elutions could be performed. While we have focused solely upon the use of DFA for the parallel screening of multiple single detergents, DFA can readily be extended to the screening of detergent mixtures, additives, ionic strength, pH and any other variable buffer components for both membrane and soluble proteins. Lastly, for proteins that possess native in vivo ligand-binding function, use of "physiological" ligand-binding affinity matrices in DFA can provide functional, as well as stability and size, characterization.

Upon inspection of FIG. 4, various detergent stability and size trends are seen for AqpZ and KcsA. We present several examples of the types of observations that can be obtained from DFA. For AqpZ, there is increased stability with an increase in detergent chain length seen with dimethylamine-N-oxide detergents (A7-A9), while decreased stability is observed with increasing ethylene chain length in the C8En detergents (E2-E4). For KcsA, increasing detergent chain length for glucoside detergents (F5-F7) resulted in decreased stability while just the addition of a hydroxyl group on Big CHAP (E12) forming Big CHAP, deoxy (F1) increases protein stability.

As mentioned in Results, FIG. 6 shows an interesting phenomenon in which the smaller KcsA tetramer (55 kDa) has a broader size distribution than that of the larger AqpZ tetramer (103 kDa). This is most likely related to the amount of detergent KcsA binds relative to AqpZ to maintain its solubility (i.e. the more bound detergent, the larger the PDC size). The observation that a higher concentration of DDM resulted in smaller PDC size for KcsA (FIG. 6, bottom panel) suggests that more detergent is required to keep KcsA in a more compact state. Because the DDM monomer concentration should be relatively constant and approximately equal to the CMC at both 1 mM and 8.5 mM DDM concentrations [15], a higher number of DDM micelles appears to be required to form a smaller PDC. Experiments, planned to investigate this phenomenon, include determination of the amount of DDM bound to KcsA as a function of DDM concentration. The amount of detergent present in the PDC can be determined by static light-scattering coupled with refractive index and UV detection [16; 17; 18; 19]. In the context of the results observed with KcsA, we note that, contrary to the most simple expectations, detergent micelle size can change as a function of detergent concentration [20; 21].

The readout from the size-stability quad-plot (e.g., FIG. 5) may help predict which detergents are best for crystallization because each quadrant represents different levels of stability and PDC size. Future experiments are planned to determine if a "crystallization-quadrant" exists. This would be somewhat analogous to the second virial coefficient ($B_{22}$) "crystallization slot" where it was demonstrated that soluble proteins with $B_{22}$ values within a specific narrow range had a propensity to form crystals [22]. Similar observations have been extended to membrane proteins [23; 24; 25; 26]. While detergents in the smallest, most stable quadrant would likely be useful for NMR, there is not enough data at present to suggest that this is necessarily the best criteria for membrane protein crystallography. Whether or not a crystallization quadrant exists, our assay and detergent panel will help with the critical "pipeline step" of choosing the proper detergents for any membrane protein of interest quickly and with minimal quantities of reagents.

The two test proteins, AqpZ and KcsA, used in this study have both had their structures determined [13; 14; 27]. What is the location in the size-stability quad-plot for the "crystallization" detergents of AqpZ and KcsA? AqpZ was crystallized in n-octyl-β-D-glucopyranoside (OG) [14; 28]. OG [F6, Table 1] is located in the second-highest stability and second-smallest size quadrant (FIG. 5). For KcsA, Doyle et al. report purification of KcsA in n-decyl-β-D-maltopyranoside (DM) followed by detergent exchange via dialysis into n-dodecyl-N,N-dimethylamine-N-oxide (LDAO) [13]. DM [G10, Table 1] is located in the second-highest stability and second-smallest size quadrant (FIG. 5). LDAO [A9, Table 1] is located in the third-highest (second-lowest) stability and smallest size quadrant (FIG. 5). As the degree of exchange is not stated, we cannot unambiguously assign accurately the "crystallization" detergent (or detergent mixture) of KcsA. However, it is interesting to note that crystal structures of KcsA:Fab complexes (e.g., [29]) have essentially all been in DM. Based upon these scant examples, it is tempting to speculate that crystallization may be best pursued from the upper-left "quarter" of the quad-plot (i.e., those detergents that lay within the more stable and smaller halves of the distribution), but such conclusions await further data.

Compared to commercial detergent panels, the detergent panel contains only those detergents that are considered non-denaturing and at concentrations that account for the varying CMC values. Furthermore, a panel as described herein is expanded compared to commercial detergent screens.

BIBLIOGRAPHY

[1] E. Granseth, D. O. Daley, M. Rapp, K. Melen, and G. von Heijne, Experimentally constrained topology models for 51,208 bacterial inner membrane proteins. J Mol Biol 352 (2005) 489-94.
[2] A. Krogh, B. Larsson, G. von Heijne, and E. L. Sonnhammer, Predicting transmembrane protein topology with a hidden Markov model: application to complete genomes. J Mol Biol 305 (2001) 567-80.
[3] E. Wallin, and G. von Heijne, Genome-wide analysis of integral membrane proteins from eubacterial, archaean, and eukaryotic organisms. Protein Sci 7 (1998) 1029-38.
[4] M. C. Wiener, Existing and emergent roles for surfactants in the three-dimensional crystallization of integral membrane proteins. Current Opinion in Colloid & Interface Science 6 (2001) 412-419.
[5] M. C. Wiener, A pedestrian guide to membrane protein crystallization. Methods 34 (2004) 364-72.
[6] P. Raman, V. Cherezov, and M. Caffrey, The Membrane Protein Data Bank. Cell Mol Life Sci 63 (2006) 36-51.
[7] S. Newstead, S. Ferrandon, and S. Iwata, Rationalizing α-helical membrane protein crystallization. Protein Sci 17 (2008) 466-472.
[8] D. A. Gutmann, E. Mizohata, S. Newstead, S. Ferrandon, V. Postis, X. Xia, P. J. Henderson, H. W. van Veen, and B. Byrne, A high-throughput method for membrane protein solubility screening: the ultracentrifugation dispersity sedimentation assay. Protein Sci 16 (2007) 1422-8.
[9] Kawate et al., Fluorescence-detection size-exclusion chromatography for precrystallization screening of integral membrane proteins. Structure 14 (2006) 673-81.
[10] G.E. Healthcare Data File: His MultiTrapFF and His Multitrap HP. 11-0036-63 AB (2007).
[11] S. Eshaghi, High-throughput expression and detergent screening of integral membrane proteins. Methods Mol Biol 498 (2009) 265-71.
[12] D. Niegowski, M. Hedren, P. Nordlund, and S. Eshaghi, A simple strategy towards membrane protein purification and crystallization. Int J Biol Macromol 39 (2006) 83-7.
[13] D. A. Doyle, J. Morais Cabral, R. A. Pfuetzner, A. Kuo, J. M. Gulbis, S. L. Cohen, B. T. Chait, and R. MacKinnon, The structure of the potassium channel: molecular basis of K+ conduction and selectivity. Science 280 (1998) 69-77.
[14] D. F. Savage, P. F. Egea, Y. Robles-Colmenares, J. D. O'Connell, 3rd, and R. M. Stroud, Architecture and selectivity in aquaporins: 2.5 a X-ray structure of aquaporin Z. PLoS Biol 1 (2003) E72.
[15] M. Zulauf, Detergent phenomena in membrane protein crystallization. in: H. Michel, (Ed.), Crystallization of Membrane Proteins, CRC Press, Boca Raton, Fla., 1991, pp. 53-72.
[16] R. A. Albright, J. L. Ibar, C. U. Kim, S. M. Gruner, and J. H. Morais-Cabral, The RCK domain of the KtrAB K+ transporter: multiple conformations of an octameric ring. Cell 126 (2006) 1147-59.
[17] Y. Hayashi, H. Matsui, and T. Takagi, Membrane protein molecular weight determined by low-angle laser light-scattering photometry coupled with high-performance gel chromatography. Methods Enzymol 172 (1989) 514-28.
[18] J. F. White, J. Grodnitzky, J. M. Louis, L. B. Trinh, J. Shiloach, J. Gutierrez, J. K. Northup, and R. Grisshammer, Dimerization of the class A G protein-coupled neurotensin receptor NTS1 alters G protein interaction. Proc Natl Acad Sci USA 104 (2007) 12199-204.
[19] D. Yernool, O. Boudker, E. Folta-Stogniew, and E. Gouaux, Trimeric subunit stoichiometry of the glutamate transporters from *Bacillus caldotenax* and *Bacillus stearothermophilus*. Biochemistry 42 (2003) 12981-8.
[20] P. G. Nilsson, H. Wennerstrom, and B. Lindman, Structure of micellar solutions of non-ionic surfactants—nuclear magnetic-resonance self-diffusion and proton relaxation studies of poly(ethylene oxide) alkyl ethers. J Phys Chem 87 (1983) 1377-1385.
[21] R. W. Roxby, and B. P. Mills, Micelle size distribution and free monomer concentration in aqueous-solutions of octyl glucoside. J Phys Chem 94 (1990) 456-459.
[22] A. George, and W. W. Wilson, Predicting protein crystallization from a dilute solution property. Acta Crystallogr D Biol Crystallogr 50 (1994) 361-5.
[23] P. J. Loll, M. Allaman, and J. Wiencek, Assessing the role of detergent-detergent interactions in membrane protein crystallization. J. Crystal Growth 232 (2001) 1-4.
[24] C. Hitscherich, J. Kaplan, M. Allaman, J. Wiencek, and P. J. Loll, Static light scattering studies of OmpF porin: implications for integral membrane proteins. Protein Sci 9 (2000) 1559-1566.
[25] B. W. Berger, C. M. Gendron, A. M. Lenhoff, and E. W. Kaler, Effects of additives on surfactant phase behavior relevant to bacteriorhodopsin crystallization. Protein Sci 15 (2006) 2682-2696.
[26] M. C. Wiener, When worlds colloid. Protein Sci 15 (2006) 2679-2681.
[27] J. Jiang, B. V. Daniels, and D. Fu, Crystal structure of AqpZ tetramer reveals two distinct Arg-189 conformations associated with water permeation through the narrowest constriction of the water-conducting channel. J Biol Chem 281 (2006) 454-60.
[28] B. V. Daniels, J. S. Jiang, and D. Fu, Crystallization and preliminary crystallographic analysis of the *Escherichia coli* water channel AqpZ. Acta Crystallogr D Biol Crystallogr 60 (2004) 561-3.
[29] Y. F. Zhou, J. H. Morais-Cabral, A. Kaufman, and R. MacKinnon, Chemistry of ion coordination and hydration revealed by a K+ channel-Fab complex at 2.0 angstrom resolution. Nature 414 (2001) 43-48.
30. Postis et al., Mol Membr Biol. 2008 December; 25(8): 617-24.
31. Tate, Practical considerations of membrane protein instability during purification and crystallisation, Methods Mol Biol. 2010; 601:187-203.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:
1. A method for determining the stability and size of a protein in at least one detergent using a rapid differential filtration detergent screening assay, said method comprising:

a) obtaining a solution comprising said protein in a first detergent;
b) adding an effective amount of an affinity resin to said solution;
c) adding an aliquot of said solution comprising said protein in a first detergent and an affinity resin to a first chamber, said first chamber comprising a filter wherein said pore size is about 0.2 µm;
d) washing said first chamber with a wash solution comprising a different detergent wherein the concentration of said different detergent is the critical micelle concentration of said different detergent;
e) eluting said protein in said first chamber with an elution solution comprising said different detergent and collecting the eluate;
f) passing an aliquot of said eluate through a second chamber comprising a high molecular weight cut-off filter and another aliquot of said eluate through a third chamber comprising a low molecular weight cut-off filter;
g) measuring the amount of protein in the eluate passing through the high molecular weight cut-off filter and the amount of protein in the eluate passing through the low molecular weight cut-off filter; and
h) comparing the amount of protein eluted through the high molecular weight cut-off filter with the amount of protein eluted through the low molecular weight cut-off filter, thereby determining the stability and size of a protein in at least one detergent using a rapid differential filtration detergent screening assay.

2. The method of claim 1, wherein said first chamber is a well of a multiwell microplate.

3. The method of claim 1, wherein said second chamber is a well of a multiwell microplate, further wherein each well comprises a high molecular weight cut-off filter.

4. The method of claim 1, wherein said third chamber is a well of a multiwell microplate, further wherein each well comprises a low molecular weight cut-off filter.

5. The method of claim 2, wherein at least two wells are used.

6. The method of claim 5, wherein the first detergent in step a) is tested with multiple different detergents in step d), wherein a different first well is used for each of said multiple different detergents tested and optionally one or more wells comprise a positive control and one or more wells comprise a negative control.

7. The method of claim 6, wherein when multiple detergents are tested, each well comprising a detergent comprises a different detergent than the other wells comprising a detergent, and optionally one or more wells comprise a positive control and one or more wells comprise a negative control.

8. The method of claim 1, wherein said high molecular weight cut-off filter is about 300 kDa.

9. The method of claim 1, wherein said low molecular weight cut-off filter is about 100 kDa.

10. The method of claim 7, wherein said multiwell plate is a 96, 384, or 1536 well plate.

11. The method of claim 10, wherein said 96 well plate is a Society for Biomolecular Sciences format plate.

12. The method of claim 10, wherein 94 different detergents are tested.

13. The method of claim 1, wherein said different detergent and said different detergents concentration is selected from the following table:

| Well | Abbrev. | Name | [Det] mM |
|---|---|---|---|
| A1 | | | |
| A2 | | | |
| A3 | Z3-12 | n-Dodecyl-N,N-dimethyl-3-ammonio-1-propanesulfonate | (2.8) |
| A4 | Z3-14 | -n-Tetradecyl-N,N-dimethyl-3-ammonio-1-propanesulfonate | (0.2) |
| A5 | DMG | n-Decyl-N,N-dimethylglycine | (19) |
| A6 | DOMG | n-Dodecyl-N,N-dimethylglycine | (1.5) |
| A7 | DAO | n-Decyl-N,N-dimethylamine-N-oxide | (10.5) |
| A8 | UDAO | n-Undecyl-N,N,-dimethylamine-N-oxide | (3.2) |
| A9 | LDAO | n-Dodecyl-N,N-dimethylamine-N-oxide | (1) |
| A10 | C-DDFOS | Cyclododecyl-1-phosphocholine | (22) |
| A11 | CF-4 | 4-Cyclohexyl-1-butylphosphocholine | (14) |
| A12 | CF-5 | 5-Cyclohexyl-1-pentylphosphocholine | (4.5) |
| B1 | CF-6 | 6-Cyclohexyl-1-hexyphosphocoline | (2.68) |
| B2 | CF-7 | 7-Cyclohexyl-1-heptylphosphocholine | (0.62) |
| B3 | FC-10 | n-Decylphosphocholine | (11) |
| B4 | FC-11 | n-Undecylphosphocholine | (1.85) |
| B5 | FC-12 | n-Dodecylphosphocholine | (1.5) |
| B6 | FC-13 | n-Tridecylphosphocholine | (0.75) |
| B7 | FC-14 | n-Tetradecylphosphocholine | (0.12) |
| B8 | FC-I11 | 2,8-Dimethyl-5-nonylphosphocholine | (26.6) |
| B9 | FC-I11-6U | Undecyl-6-phosphocholine | (25.8) |
| B10 | FC-I9 | 2,6-Dimethyl-4-heptylphosphocholine | (32) |
| B11 | FC-U10-11 | 10-Undecylenyl-1-phosphocholine | (6.2) |
| B12 | DHPC | 1,2-Diheptanoyl-sn-glycero-3-phosphocholine | (1.4) |
| C1 | LPC-10 | 1-Decanoyl-2-hydroxy-sn-glycero-3-phosphocholine | (8) |
| C2 | LPC-12 | 1-Lauroyl-2-hydroxy-sn-glycero-3-phosphocholine | (0.7) |
| C3 | FOSFEN-9 | Nonylphenylphosphocholine | (1.35) |
| C4 | CHAPS | 3-[(3-Cholamidopropyl)dimethylamminio]-1-propanesulfonate | (8) |
| C5 | CHAPSO | 3-[(3-Cholamidopropyl)dimethylamminio]-2-hydroxy-1-propanesulfonate | (8) |
| C6 | DDMAU | n-Dodecyl-N,N-(dimethylammonio)undecanoate | (0.13) |
| C7 | DDMAB | n-Dodecyl-N,N-(dimethylammonio)butyrate | (4.3) |
| C8 | LAPAO | 3-Dpdecylamido-N,N'-dimethylpropyl amine oxide | (1.6) |
| C9 | TRIPAO | 3-(3 Butyl-3-phenylheptanamido)-N,N-dimethylpropan-1-amine oxide | (4.5) |
| C10 | T-20 | Polyoxyethylene(20) sorbitane monolaurate | (0.059) |
| C11 | BRIJ-35 | Polyoxyethylene lauryl ether | (0.091) |
| C12 | TX-100 | Tetramethylbutyl)phenyl]-ω-hydroxy-poly(oxy-1,2-ethanediyl), average MW 647 | (0.23) |
| D1 | TX-114 | Teteamethylbutyl)phenyl]-ω-hydroxy-poly(oxy-1,2-ethanediyl), average MW 536 | (0.2) |
| D2 | TX-305 | Teteamethylbutyl)phenyl]-ω-hydroxy-poly(oxy-1,2-ethanediyl), average MW 1526 | (0.65) |
| D3 | TX-405 | Teteamethylbutyl)phenyl]-ω-hydroxy-poly(oxy-1,2-ethanediyl), average MW 1967 | (0.81) |
| D4 | NID-P40 | [Octylphenoxy]polyethoxyethanol | (0.3) |
| D5 | APO8 | Dimethyloctylphosphine oxide | (40) |
| D6 | APO9 | Dimethylnonylphosphine oxide | (10) |
| D7 | APO10 | Dimethyldecylphosphine oxide | (4.66) |
| D8 | APO11 | Dimethylundecylphosphine oxide | (1.2) |
| D9 | APO12 | Dimethyldodecylphosphine oxide | (0.57) |
| D10 | C6E3 | Triethylene glycol monohexyl ether | (23) |
| D11 | C6E4 | Tetraethylene glycol monohexyl ether | (30) |
| D12 | C6E5 | Pentaethylene glycol monohexyl ether | (37) |
| E1 | C7E5 | Pentaethylene glycol monoheptyl ether | (21) |
| E2 | C8E4 | Tetraethylene glycol monooctyl ether | (8) |
| E3 | C8E5 | Pentaethylene glycol monooctyl ether | (7.1) |
| E4 | C8E6 | Hexaethylene glycol monooctyl ether | (10) |
| E5 | C10E5 | Pentaethylene glycol monodecyl ether | (0.81) |
| E6 | C10E6 | Hexaethylene glycol monodecyl ether | (0.9) |
| E7 | C10E9 | Polyoxyethylene(9)decyl ether | (1.3) |
| E8 | C12E8 | Octaethylene glycol monododecyl ether | (0.09) |
| E9 | C12E9 | Polyoxyethylene(9)dodecyl ether | (0.05) |
| E10 | C12E10 | Polyoxyethylene(10)dodecyl ether | (0.2) |
| E11 | C13E8 | Polyoxyethylene(8)tridecyl ether | (0.1) |
| E12 | CHAP | N,N'-bis-(3-D-Gluconamidopropyl)cholamide | (2.9) |

-continued

| Well | Abbrev. | Name | [Det] mM |
|---|---|---|---|
| F1 | CHAP-D | N,N'-bis-(3-D-Gluconamidopropyl)deoxycholamide | (1.4) |
| F2 | OHES | Octyl-2-hydroxyethyl-sulfoxide | (24.2) |
| F3 | RDHPOS | Rac-2,3-dihydroxypropyloctylsulfoxide | (24.2) |
| F4 | GX-100 | Polyoxyethylene(10) Isotridecyl Ether | (0.15) |
| F5 | HTG | n-Heptyl-β-D-thioglucopyranoside | (29) |
| F6 | OG | n-Octyl-β-D-glucopyranoside | (18) |
| F7 | NG | n-Nonyl-β-D-glucopyranoside | (6.5) |
| F8 | CYGLU-3 | 3-Cyclohexyl-1-propyl-β-D-glucoside | (28) |
| F9 | HECAMEG | Methyl-6-O-(N-heptylcarbamoyl)-α-D-glucopyranoside | (19.5) |
| F10 | HEGA-9 | Nonanoyl-N-hydroxyethylglucamide | (39) |
| F11 | C-HEGA-10 | Cyclohexylbutanoyl-N-hydroxyethylglucamide | (35) |
| F12 | C-HEGA-11 | Cyclohexylbutanoyl-N-hydroxyethylglucamide | (11.5) |
| G1 | CYMAL-3 | 3-Cyclohexyl-1-propyl-β-D-maltoside | (30) |
| G2 | CYMAL-4 | 4-Cyclohexyl-1-butyl-β-D-maltoside | (7.6) |
| G3 | CYMAL-5 | 5-Cyclohexyl-1-pentyl-β-D-maltoside | (2.4) |
| G4 | CYMAL-6 | 6-Cyclohexyl-1-hexyl-β-D-maltoside | (0.56) |
| G5 | CYMAL-7 | 7-Cyclohexyl-1-heptyl-β-D-maltoside | (0.19) |
| G6 | DMHM | 2,6-Dimethyl-4-heptyl-β-D-maltoside | (27.5) |
| G7 | OM | n-Octyl-β-D-maltopyranoside | (19.5) |
| G8 | NM | n-Nonyl-β-D-maltopyranoside | (6) |
| G9 | DαM | n-Decyl-α-D-maltopyranoside | (1.6) |
| G10 | DM | n-Decyl-β-D-maltopyranoside | (1.8) |
| G11 | UDαM | n-Undecyl-α-D-maltopyranoside | (0.58) |
| G12 | UDM | n-Undecyl-β-D-maltopyranoside | (0.59) |
| H1 | ωUDM | ω-Undecylenyl-β-D-maltopyranoside | (1.2) |
| H2 | DDαM | n-Dodecyl-α-D-maltopyranoside | (0.15) |
| H3 | DDM | n-Dodecyl-β-D-maltopyranoside | (0.17) |
| H4 | TDM | n-Tridecyl-β-D-maltopyranoside | (0.03) |
| H5 | OTM | n-Octyl-β-D-thiomaltopyranoside | (8.5) |
| H6 | NTM | n-Nonyl-β-D-thiomaltopyranoside | (3.2) |
| H7 | DTM | n-Decyl-β-D-thiomaltopyranoside | (0.9) |
| H8 | UDTM | n-Undecyl-β-D-thiomaltopyranoside | (0.21) |
| H9 | DDTM | n-Dodecyl-β-D-thiomaltopyranoside | (0.05) |
| H10 | S-8 | n-Octanoyl-β-D-fructofuranosyl-α-D-glucopyranoside | (24.4) |
| H11 | S-10 | α-D-Glucopryanoside, β-D-Fructofuranosyl Monodecanoate | (2.5) |
| H12 | S-12 | n-Monododecanoate-α-D-glucopyranoside, β-D-Fructofuranosyl. | (0.3) |

14. The method of claim 1, wherein said solution comprising said protein in a first detergent comprises about 1000 micrograms or less of said protein.

15. The method of claim 1, wherein said solution comprising said protein in a first detergent comprises about 500 micrograms or less of said protein.

16. The method of claim 1, wherein said solution comprising said protein in a first detergent comprises about 400 micrograms or less of said protein.

17. The method of claim 1, wherein said solution comprising said protein in a first detergent comprises about 200 micrograms or less of said protein.

18. The method of claim 1, wherein said solution comprising said protein in a first detergent comprises about 100 micrograms or less of said protein.

19. The method of claim 1, wherein said solution comprising said protein in a first detergent comprises about 50 micrograms or less of said protein.

20. The method of claim 1, wherein said method is performed in less than about two hours.

21. The method of claim 1, wherein said method is performed in less than about 1 hour.

22. The method of claim 1, wherein said protein amounts are determined by dot blot or Western blot analysis.

23. The method of claim 22, wherein said protein amounts determined from the high molecular weight cut-off dot blots are normalized and plotted with the ratio of low:high normalized intensities and the values grouped into quartiles.

24. The method of claim 22, wherein said protein amounts determined from the high molecular weight cut-off dot blots are normalized and plotted graphically on the abscissa while the ratio of low:high normalized intensities are plotted on the ordinate.

25. The method of claim 1, further wherein said method is used to screen detergent mixtures, additives, ionic strength, and pH.

26. The method of claim 1, wherein said protein is a membrane protein.

27. The method of claim 1, wherein said different detergent has zwitterionic or nonionic headgroups.

28. The method of claim 1, wherein at least one of said first, second, or third chambers is subjected to centrifugation to enhance the filtration process.

* * * * *

UNITED STATES PATENT AND TRADEMARK OFFICE
CERTIFICATE OF CORRECTION

PATENT NO. : 9,606,126 B2  
APPLICATION NO. : 13/376729  
DATED : March 28, 2017  
INVENTOR(S) : Michael C. Wiener and James M. Vergis Page 1 of 1

It is certified that error appears in the above-identified patent and that said Letters Patent is hereby corrected as shown below:

On the Title Page

Item (73) Assignee:  
Replace "University of Virgina Patent Foundation"  
With --University of Virginia Patent Foundation--

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*